United States Patent [19]

Rheinheimer et al.

[11] Patent Number: 5,783,521

[45] Date of Patent: Jul. 21, 1998

[54] SUBSTITUTED PYRIDYLSALICYLALDEHYDE OR -SALICYLIC ACID DERIVATIVES, THEIR PREPARATION AND THEIR USE AS HERBICIDES

[75] Inventors: Joachim Rheinheimer; Uwe Josef Vogelbacher, both of Ludwigshafen; Ernst Baumann, Dudenhofen; Matthias Gerber, Limburgerhof; Karl-Otto Westphalen, Speyer; Helmut Walter, Obrigheim, all of Germany

[73] Assignee: BASF Aktiengesellschaft, Ludwigshafen, Germany

[21] Appl. No.: 332,723

[22] Filed: Nov. 1, 1994

[51] Int. Cl.⁶ .................... C07D 403/12; A01N 43/54
[52] U.S. Cl. .................... 504/272; 504/243; 504/240; 504/241; 544/278; 544/253; 544/300; 544/310; 544/316
[58] Field of Search .................... 544/253, 278, 544/300, 310, 316; 504/242, 243, 240, 241

[56] References Cited

U.S. PATENT DOCUMENTS

| | | | |
|---|---|---|---|
| 5,085,686 | 2/1992 | Vogelbacher | 71/92 |
| 5,100,458 | 3/1992 | Eicken et al. | 71/92 |
| 5,149,357 | 9/1992 | Dixson et al. | 71/92 |
| 5,186,734 | 2/1993 | Andree et al. | 504/196 |
| 5,290,755 | 3/1994 | Vogelbacher et al. | 504/242 |

FOREIGN PATENT DOCUMENTS

| | | |
|---|---|---|
| 061913 | 10/1982 | European Pat. Off. |
| 91/13065 | 9/1991 | WIPO |
| 94/22310 | 10/1994 | WIPO |

OTHER PUBLICATIONS

Murugesan et al; Chemical Abstracts, vol. 115:256220 (1991).
Chem. Abstr., vol. 119, No. 15, Oct. 11, 1993, abstract No. 160312g, Wada et al., Preparation of (carboxyphenoxy)pyrimidines as herbicides), p. 939. (English abstract of JP–A 05 032 639).

Primary Examiner—John M. Ford
Attorney, Agent, or Firm—Keil & Weinkauf

[57] ABSTRACT

Substituted pyridylsalicylaldehyde and —salicylic acid derivatives of the formula I

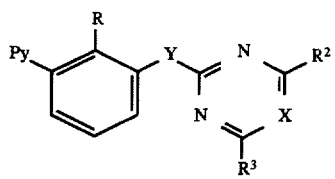

where R is a formyl group, a $CO_2H$ group or a radical which can be hydrolyzed to $CO_2H$ and the other substituents have the following meanings:

$R^2$ is halogen, alkyl, haloalkyl, alkoxy, haloalkoxy or alkylthio;

X is nitrogen or $CR^{13}$, $R^{13}$ being hydrogen or halogen or together with $R^3$ forming a 3- to 4-membered alkylene or alkenylene chain in which at least one methylene group is replaced by oxygen;

$R^3$ is halogen, alkyl, haloalkyl, alkoxy, haloalkoxy or alkylthio, or $R^3$ is linked with $R^{13}$ as indicated above to give a 5- or 6-membered ring;

Y is oxygen or sulfur;

Py is a substituted pyridine ring, are described.

6 Claims, No Drawings

SUBSTITUTED PYRIDYLSALICYLALDEHYDE OR -SALICYLIC ACID DERIVATIVES, THEIR PREPARATION AND THEIR USE AS HERBICIDES

The present invention relates to substituted pyridylsalicylaldehyde and —salicylic acid derivatives of the formula I

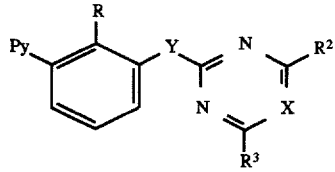

where R is a formyl group, a $CO_2H$ group or a radical which can be hydrolyzed to give $CO_2H$ and the other substituents have the following meanings:

$R^2$ is halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

X is nitrogen or $CR^{13}$, $R^{13}$ being hydrogen or halogen or together with $R^3$ forming a 3- to 4-membered alkylene or alkenylene chain in which one methylene group in each case is replaced by oxygen;

$R^3$ is halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, or $R^3$ is linked with $R^{13}$ as indicated above to give a 5- or 6-membered ring;

Y is oxygen or sulfur;

Py is a pyridine ring linked in any desired position, which carries four substituents $R^{14}$, $R^{15}$, $R^{16}$ and $R^{17}$;

$R^{14}$ is a) a $C_3$–$C8$-cycloalkyl group, which can carry one to three $C_1$–$C_4$-alkyl radicals;

b) a $C_1$–$C_8$-alkyl group which can carry one to five halogen atoms and carries one of the following radicals:

$C_1$–$C_4$-alkoxy, $C_1$–$C_4$-haloalkoxy, $C_1$–$C_4$-alkylthio, cyano, $C_3$–$C_8$-cycloalky or di-$C_1$–$C_4$-alkylamino;

c) a $C_1$–$C_8$-alkoxy group, which can carry one to five halogen atoms and/or one of the following radicals:

$C_1$–$C_4$-alkoxy, $C_1$–$C_4$-haloalkoxy, $C_1$–$C_4$-alkylthio, cyano, $C_3$–$C_8$-cycloalkyl or di-$C_1$–$C_4$-alkylamino;

d) a $C_1$–$C_4$-alkylthio group, which can carry one to five halogen atoms and/or one of the following radicals:

$C_1$–$C_4$-alkoxy, $C_1$–$C_4$-haloalkoxy, $C_1$–$C_4$-alkylthio, cyano, $C_3$–$C_8$-cycloalkyl or di-$C_1$–$C_4$-alkylamino;

e) a di-$C_1$–$C_4$-alkylamino group or a di-$C_1$–$C_4$-alkylaminoxy group;

f) a $C_2$–$C_6$-alkenyl group or a $C_2$–$C_6$-alkynyl group, which can carry one to five halogen atoms and/or one of the following radicals:

$C_1$–$C_4$-alkoxy, $C_1$–$C_4$-haloalkoxy or $C_1$–$C_4$-alkylthio;

$R^{15}$, $R^{16}$ and $R^{17}$ are in each case independently of one another hydrogen, nitro, halogen, $C_1$–$C_8$-alkyl, $C_1$–$C_8$-haloalkyl and the radicals mentioned for $R^{14}$.

According to the prior art, eg. WO 91/13065 and DE-A 39 19 435, salicylaldehyde and salicylic acid derivatives having an unsubstituted pyridyl radical show a herbicidal action. In the last-mentioned specification, corresponding compounds containing specifically substituted pyridyl radicals such as 6-methyl-2-pyridyl, 3-chloro-5-pyridyl and 5-chloro-2-pyridyl are also disclosed. The action of the compounds known from the literature is not always satisfactory with respect to herbicidal action, the bioregulatory action and/or selectivity.

It is therefore an object of the invention to make available pyridyl-substituted salicylaldehyde and —salicylic acid derivatives having improved action.

We have now found that this object is achieved by the pyridine derivatives I defined at the outset. The novel compounds I show an excellent herbicidal action with, to some extent, improved selectivity to crop plants.

We have also found processes and novel intermediates for preparing the compounds I and their use as herbicides and growth regulators.

In the description, the substituents mentioned below have the preferred following meanings:

$C_1$–$C_4$-alkyl: methyl, ethyl, 1-propyl, 2-propyl, 2-methyl-2-propyl, 2-methyl-1-propyl, 1-butyl, 2-butyl;

$C_1$–$C_8$-alkyl: $C_1$–$C_4$-alkyl and also pentyl, 1-methylbutyl, 2-methyl-butyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl;

$C_1$–$C_2$-haloalkyl: fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl and pentafluoroethyl;

$C_1$–$C_2$-haloalkoxy: difluoromethoxy, trifluoromethoxy, chlorodifluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy;

$C_1$–$C_4$-alkoxy: methoxy, ethoxy, propoxy, 1-methylethoxy, butoxy, 1-methylpropoxy, 2-methylpropoxy, 1,1-dimethylethoxy, in particular methoxy, ethoxy, 1-methylethoxy;

$C_1$–$C_4$-alkylthio: methylthio, ethylthio, propylthio, 1-methylethylthio, butylthio, 1-methylpropylthio, 2-methylpropylthio, 1,1-dimethylethylthio, in particular methylthio and ethylthio;

$C_3$–$C_6$-alkenyl: 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl- 3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl;

$C_3$–$C_6$-alkynyl: 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl.

The radical R is widely variable with respect to the radicals which can be hydrolyzed to the carboxyl group. For example, R is a group

where $R^1$ has the following meanings:

a) hydrogen;

b) a succinylimidoxy group;

c) a 5-membered heteroaromatic linked via a nitrogen atom, such as pyrrolyl, pyrazolyl, imidazolyl or triazolyl, which can carry one to two halogen atoms, in particular fluorine and chlorine, and/or one to two of the following radicals:
$C_1$–$C_4$-alkyl; $C_1$–$C_4$-haloalkyl, in particular $C_1$–$C_2$-haloalkyl;
$C_1$–$C_4$-haloalkoxy, in particular $C_1$–$C_2$-haloalkoxy;
$C_1$–$C_4$-alkoxy;
$C_1$–$C_4$-alkylthio;

d) $R^1$ is additionally a radical —$(O)_m$-$NR^6R^7$, where m is 0 or 1 and $R^6$ and $R^7$, which can be identical or different, have the following meanings:
hydrogen;
$C_1$–$C_8$-alkyl, in particular $C_1$–$C_4$-alkyl;
$C_3$–$C_6$-alkenyl, in particular 2-propenyl, 2-butenyl, 3-methyl-2-butenyl and 3-methyl-2-pentenyl;
$C_3$–$C_6$-alkynyl, preferably 2-propynyl, 2-butynyl, 1-methyl-2-propynyl and 1-methyl-2-butynyl, in particular 2-propynyl;
$C_3$–$C_8$-cycloalkyl such as cyclopropyl, cyclobutyl, cyclopentyl, cyclohexyl, cycloheptyl and cyclooctyl, these alkyl, cycloalkyl, alkenyl and alkynyl groups in each case being able to carry one to five, in particular one to three, halogen atoms, preferably fluorine or chlorine, and/or one to two of the following groups:
$C_1$–$C_4$-alkyl, $C_1$–$C_4$-alkoxy, $C_1$–$C_4$-alkylthio, $C_1$–$C_4$-haloalkoxy, $C_3$–$C_6$-alkenyloxy, $C_3$–$C_6$-alkenylthio, $C_3$–$C_6$-alkynyloxy, $C_3$–$C_6$-alkynylthio, the alkenyl and alkynyl constituents present in these radicals preferably having the abovementioned meanings;
$C_1$–$C_4$-alkylcarbonyl such as, in particular, methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl;
$C_1$–$C_4$-alkoxycarbonyl such as methoxycarbonyl, ethoxycarbonyl, propyloxycarbonyl, 1-methylethoxycarbonyl, butyloxycarbonyl, 1-methylpropyloxycarbonyl, 2-methylpropyloxycarbonyl, 1,1-dimethylethoxycarbonyl;

$C_3$–$C_6$-alkenylcarbonyl, $C_3$–$C_6$-alkynylcarbonyl, $C_3$–$C_6$-alkenyloxycarbonyl and $C_3$–$C_6$-alkynyloxycarbonyl, the alkenyl and alkynyl radicals preferably being defined as above;

phenyl, unsubstituted or mono- or polysubstituted by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio such as, for example, 2-fluorophenyl, 3-chlorophenyl, 4-bromophenyl, 2-methylphenyl, 3-nitrophenyl, 4-cyanophenyl, 2-trifluoromethylphenyl, 3-methoxyphenyl, 4-trifluoroethoxyphenyl, 2-methylthiophenyl, 2,4-dichlorophenyl, 2-methoxy-3-methylphenyl, 2,4-dimethoxyphenyl, 2-nitro-5-cyanophenyl, 2,6-difluorophenyl;

di-($C_1$–$C_4$-alkyl)amino such as, in particular, dimethylamino, diethylamino, dipropylamino, N-propyl-N-methylamino, N-propyl-N-ethylamino, diisopropylamino, N-isopropyl-N-methylamino, N-isopropyl-N-ethylamino, N-isopropyl-N-propylamino;

$R^6$ and $R^7$ additionally are phenyl, which can be substituted by one or more of the following radicals: halogen, nitro, cyano, $C_1$–$C_4$-alkyl, $C_1$–$C_4$-haloalkyl, in particular $C_1$–$C_2$-haloalkyl, $C_1$–$C_4$-alkoxy, $C_1$–$C_4$-haloalkoxy, in particular $C_1$–$C_2$-haloalkoxy, or $C_1$–$C_4$-alkylthio;

or $R^6$ and $R^7$ together form an unsubstituted or substituted $C_4$–$C_7$-alkylene chain closed to give a ring, which can contain a heteroatom selected from the group consisting of oxygen, sulfur and nitrogen, such as —$(CH_2)_4$—, —$(CH_2)_5$—, —$(CH_2)_6$—, —$(CH_2)_7$—, —$(CH_2)_2$—O—$(CH_2)_2$—, —$CH_2$—S—$(CH_2)_3$—, —$(CH_2)_2$—O—$(CH_3)_3$—NH—$(CH_2)_3$—, —$CH_2$—NH—$(CH_2)_2$—, —$CH_2$—CH=CH—$CH_2$—, —CH=CH—$(CH_2)_3$—, suitable substituents in particular being $C_1$–$C_4$-alkyl radicals;

e) $R^1$ is additionally a group

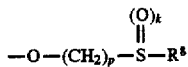

where k assumes the values 0, 1 or 2, p assumes the values 1, 2, 3 or 4 and $R^8$ is $C_1$–$C_4$-alkyl, $C_1$–$C_4$-haloalkyl, $C_3$–$C_6$-alkenyl, $C_3$–$C_6$-alkynyl or unsubstituted or substituted phenyl, as mentioned in particular for $R^6$ and $R^7$;

f) $R^1$ additionally is a radical $OR^9$, where $R^9$ is:

i) hydrogen, the cation of an alkali metal or the cation of an alkaline earth metal, such as lithium, sodium, potassium, calcium, magnesium or barium, or an environmentally tolerable organic ammonium ion such as tert-$C_1$–$C_4$-alkylammonium or ammonium [$NH_4^+$];

ii) $C_3$–$C_8$-cycloalkyl as mentioned above, which can carry one to three $C_1$–$C_4$-alkyl groups, in particular cyclopropyl, cyclopentyl, cyclohexyl or methylcyclohexyl;

iii) $C_1$–$C_8$-alkyl, which can carry one to five halogen atoms, in particular fluorine and chlorine and/or one of the following radicals:
$C_1$–$C_4$-alkoxy, $C_1$–$C_4$-alkylthio, cyano, $C_1$–$C_4$-alkylcarbonyl, $C_3$–$C_8$-cycloalkyl, $C_1$–$C_4$-alkoxycarbonyl, phenyl, or phenyl or phenoxy which is mono- or polysubstituted by halogen, nitro, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio, in particular as mentioned above;

iv) a $C_1$–$C_8$-alkyl group, which can carry one to five, preferably one to three, halogen atoms, in particular fluorine and/or chlorine, and carries one of the following radicals: a 5-membered heteroaromatic, containing one to three nitrogen atoms, or a 5-membered heteroaromatic, containing one nitrogen atom and an oxygen or sulfur atom, such as pyrazolyl, imidazolyl, benzimidazolyl, triazolyl, benzotriazolyl, isoxazolyl, oxazolyl or thiazolyl, bonded via a C atom or, if possible, an N atom, the heteroaromatic being able to carry one to four halogen atoms and/or one to two of the following radicals:

nitro, cyano, $C_1$–$C_4$-alkyl, $C_1$–$C_4$-haloalkyl, $C_1$–$C_4$-alkoxy, phenyl, $C_1$–$C_4$-haloalkoxy and/or $C_1$–$C_4$-alkylthio. The following may be mentioned in particular: 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 1-imidazolyl, 1-benzimidazolyl, 1,2,4-triazol-1-yl, 3-methyl-1,2,4-triazol-1-yl, 5-methyl-1,2,4-triazol-1-yl, 1-benzotriazolyl, 3-isopropylisoxazol-5-yl, 3-methylisoxazol-5-yl, oxazol-2-yl, thiazol-2-yl, imidazol-2-yl, 3-ethylisoxazol-5-yl, 3-phenyl- isoxazol-5-yl, 3-tert-butylisoxazol-5-yl;

v) a $C_2$–$C_6$-alkyl group, which in the 2-position carries one of the following radicals: $C_1$–$C_4$-alkoxyimino, $C_3$–$C_6$-alkynyloxyimino, $C_3$–$C_6$-haloalkenyloxyimino or benzyloxyimino;

vi) a $C_3$–$C_6$-alkenyl group or a $C_3$–$C_6$-alkynyl group, these groups in turn being able to carry one to five halogen atoms;

vii) $R^9$ additionally is a phenyl radical, which can carry one to five halogen atoms and/or one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio, in particular as mentioned above;

viii) a 5-membered heteroaromatic linked via a nitrogen atom, containing one to three nitrogen atoms, such as pyrazolyl, imidazolyl, benzimidazolyl, triazolyl or benzotriazolyl, preferably bonded via the 1-position, the heteroaromatic being able to carry one to two halogen atoms and/or one to two of the following radicals:

$C_1$–$C_4$-alkyl, $C_1$–$C_4$-haloalkyl, $C_1$–$C_4$-alkoxy, phenyl, $C_1$–$C_4$-haloalkoxy and/or $C_1$–$C_4$-alkylthio. The following may be mentioned in particular: 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 1-imidazolyl, 1-benzimidazolyl, 1,2,4-triazol-1-yl, 3-methyl-1,2,4-triazol-1-yl, 5-methyl-1,2,4-triazol-1-yl, 1-benzotriazolyl, 3,4-dichloroimidazol-1-yl;

ix) $R^9$ is additionally a group —N=$CR^{10}R^{11}$, where $R^{10}$ and $R^{11}$, which can be identical or different, are:

$C_1$–$C_{12}$-alkyl, in particular $C_1$–$C_8$-alkyl, $C_3$–$C_6$-alkenyl, $C_3$–$C_6$-alkynyl or $C_3$–$C_8$-cycloalkyl, these radicals being able to carry a $C_1$–$C_4$-alkoxy or $C_1$–$C_4$-alkylthio radical and/or an unsubstituted or substituted phenyl radical, in particular as mentioned above;

phenyl, which can be substituted by one or more of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio, these radicals in particular corresponding to those mentioned above for $R^1$;

or $R^{10}$ and $R^{11}$ together form a $C_3$–$C_{12}$-alkylene chain, which can carry one to three $C_1$–$C_4$-alkyl groups and can contain a heteroatom from the group consisting of oxygen, sulfur and nitrogen, in particular as mentioned in the case of $R^6$ and $R^7$;

g) $R^1$ is additionally a radical —NH—$SO_2$—$R^{12}$, where $R^{12}$ is:

$C_1$–$C_4$-alkyl, $C_3$–$C_6$-alkenyl, $C_3$–$C_6$-alkynyl or $C_3$–$C_8$-cycloalkyl, in particular as mentioned above for R1, these radicals being able to carry a $C_1$–$C_4$-alkoxy or $C_1$–$C_4$-alkylthio radical and/or a phenyl radical as mentioned above;

unsubstituted or substituted phenyl, in particular as mentioned above.

Particularly preferably, $R^1$ is an $OR^9$ group.

With respect to the biological action, active compounds of the formula I are preferred in which the other substituents have the following meanings:

$R^2$ is the $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio groups and halogen atoms mentioned specifically for $R^1$, in particular chlorine, fluorine, methyl, methoxy, ethoxy, difluoromethoxy, trifluoromethoxy and trifluoromethyl, particularly preferably methoxy;

X is nitrogen or $CR^{13}$, where $R^{13}$ is preferably hydrogen or halogen such as fluorine or chlorine, or together with $R^3$ is a 4- to 5-membered alkylene or alkenylene chain, in which one methylene group in each case is replaced by oxygen, such as —$CH_2$—$CH_2$—O—, —CH=CH—O—, —$CH_2$—$CH_2$—$CH_2$—O—, —CH=CH—$CH_2O$—, in particular hydrogen, fluorine and —$CH_2$—$CH_2$—O—;

$R^3$ is $C_1$–$C_4$-alkyl, $C_1$–$C_4$-haloalkyl, in particular $C_1$–$C_2$-haloalkyl, $C_1$–$C_4$-alkoxy, $C_1$–$C_4$-haloalkoxy, in particular $C_1$–$C_2$-haloalkoxy, $C_1$–$C_4$-alkylthio groups, in particular fluorine, trifluoromethyl, chlorine, methyl, methoxy, ethoxy, difluoromethoxy or trifluoromethoxy, particularly preferably methoxy, or is linked with $R^{13}$ as mentioned above to give a 5- or 6-membered ring;

Py is a pyridine ring linked in the 2-, 3- or 4-position, which carries four substituents $R^{14}$, $R^{15}$, $R^{16}$ and $R^{17}$ in any desired position;

$R^{14}$ is a) a $C_3$–$C_8$-cycloalkyl group, which can carry one to three $C_1$–$C_4$-alkyl radicals, in particular cyclopropyl, cyclopentyl, cyclohexyl or methylcyclohexyl;

b) a $C_1$–$C_8$-alkyl group, which can carry one to five halogen atoms and one of the following radicals:

$C_1$–$C_4$-alkoxy, $C_1$–$C_4$-haloalkoxy, particularly $C_1$–$C_2$-haloalkoxy, $C_1$–$C_4$-alkylthio, cyano, $C_3$–$C_8$-cycloalkyl or di-$C_1$–$C_4$-alkylamino, particularly preferably 2-methoxyethyl, 2-ethoxyethyl, 2-dimethylaminoethyl, 2-diethylaminoethyl, methoxymethyl, ethoxymethyl, dimethylaminomethyl, diethylaminomethyl, c) a $C_1$–$C_8$-alkoxy group, which can carry one to five halogen atoms and/or one of the following radicals:

$C_1$–$C_4$-alkoxy, $C_1$–$C_4$-haloalkoxy, particularly $C_1$–$C_2$-haloalkoxy, $C_1$–$C_4$-alkylthio, cyano, $C_3$–$C_8$-cycloalkyl or di-$C_1$–$C_4$-alkylamino, particularly preferably 2-methoxyethoxy, 2-ethoxyethoxy, 2-dimethylaminoethoxy, 2-diethylaminoethoxy, methoxymethoxy, ethoxymethoxy, dimethylaminomethoxy, diethylaminomethoxy, 2-methylthioethoxy, 2,2,2-trifluoroethoxy, methoxy, ethoxy, propoxy, 2-propoxy;

d) a $C_1$–$C_4$-alkylthio group, which can carry one to five halogen atoms and/or one of the following radicals: $C_1$–$C_4$-alkoxy, $C_1$–$C_4$-haloalkoxy, $C_1$–$C_4$-alkylthio, cyano, $C_3$–$C_8$-cycloalkyl or di-$C_1$–$C_4$-alkylamino, particularly preferably methylthio, ethylthio, propylthio, 2-propylthio, methoxymethylthio;

e) a di-($C_1$–$C_4$-alkyl)amino group or a di-($C_1$–$C_4$-alkyl) aminoxy group, particularly preferably dimethylamino, diethylamino, N-methyl-N-ethylamino, diisopropylamino, dipropylamino, dimethylaminoxy, diethylaminoxy;

f) a $C_2$–$C_6$-alkenyl group or a $C_2$–$C_6$-alkynyl group, which can carry one to five halogen atoms and/or one of the following radicals:
$C_1$–$C_4$-alkoxy, $C_1$–$C_4$-haloalkoxy or $C_1$–$C_4$-alkylthio, particularly preferably vinyl, 2-propenyl, ethynyl, 1-propynyl, 3-propynyl, 3-methoxy-1-propynyl, chloroallyl;

$R^{15}$, $R^{16}$ and $R^{17}$ are the radicals mentioned under $R^{14}$ and also hydrogen, nitro, $C_1$–$C_8$-alkyl, $C_1$–$C_2$-haloalkyl, particularly preferably hydrogen, $C_1$–$C_4$-alkyl, halogen such as, in particular, fluorine or chlorine, $C_1$–$C_2$-haloalkyl, $C_1$–$C_4$-alkoxy, $C_1$–$C_2$- haloalkoxy or $C_1$–$C_4$-alkylthio.

Substituted pyridylsalicylaldehyde and -salicylic acid derivatives of the formula I as claimed in claim 1, where at least two of the radicals $R^{15}$ to $R^{17}$ are hydrogen, are particularly preferred.

Compounds of the formula I are additionally preferred where $R^3$ is methoxy and X is CH or CF, or where $R^3$, together with X, forms an $OCH_2CH_2$ chain.

Aromatic carboxylic acid derivatives of the formula I are obtained, for example, by reacting a corresponding aromatic carboxylic acid derivative of the formula II

which is accessible according to the examples mentioned further below, with an appropriate compound of the formula III

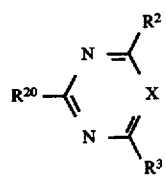

in the presence of a base.

$R^{20}$ is chlorine, bromine, iodine, aryl- or alkylsulfonyl such as eg. toluenesulfonyl or methylsulfonyl or another equivalent leaving group. Compounds of the formula IV having a reactive substituent $R^{20}$ are known in most cases or easy to obtain using general technical knowledge. The bases used are alkali metal or alkaline earth metal hydrides such as NaH or $CaH_2$, alkali metal hydroxides such as NaOH or KOH, alkali metal alkoxides such as potassium tert-butoxide, alkali metal carbonates such as $Na_2CO_3$ or $K_2CO_3$, alkali metal amides such as $NaNH_2$ or lithium diisopropylamide or tertiary amines such as triethylamine or pyridine. When using an inorganic base, a phase-transfer catalyst can be added if this promotes the conversion. Crown ethers or organic ammonium compounds, for example, are suitable for this.

Many of the customary solvents can be used, such as, for example, dimethyl sulfoxide, dimethylformamide, tetrahydrofuran, methyl t-butyl ether, diethyl ether, acetone, methyl ethyl ketone, toluene, benzene, dimethoxyethane, dioxane, pyridine or t-butanol.

In general, the reaction temperatures are from –80° to 150° C., preferably from –10° to 130° C.

A further advantageous preparation route for the compounds I consists in reacting cyclic acetals of the formula IV

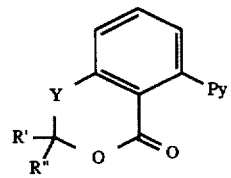

where the substituents have the following meanings:

R' and R" are hydrogen;

$C_1$–$C_4$-alkyl, this radical in each case being able to carry one to five halogen atoms and/or one to two $C_1$–$C_4$-alkoxy groups;

phenyl, this radical in each case being able to carry one to five halogen atoms and/or one to two of the following groups: $C_1$–$C_4$-alkyl, $C_1$–$C_4$-alkoxy, $C_1$–$C_4$-haloalkyl or nitro;

additionally the two radicals together are a $C_2$–$C_6$-alkylene chain, which can be substituted by one to five halogen atoms and/or $C_1$–$C_4$-alkyl radicals;

Y is oxygen or sulfur;

with a salt of the formula V

where M is an alkali metal cation such as lithium, sodium, potassium or an equivalent of an alkaline earth metal cation such as magnesium, calcium or barium and where $R^{1''}$ corresponds to a subset of $R^1$ and has the following meanings:

a) a 5-membered heteroaromatic linked via a nitrogen atom and containing two to three nitrogen atoms, which can carry one to two halogen atoms and/or one to two of the following radicals:
$C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

b) a radical —$(O)_m$—$NR^6R^7$,
where m is 0 or 1 and $R^6$ and $R^7$, which can be identical or different, have the following meanings:
hydrogen;
$C_1$–$C_8$-alkyl, $C_3$–$C_6$-alkenyl, $C_3$–$C_6$-alkynyl, $C_3$–$C_8$-cycloalkyl, these radicals in each case being able to carry one to five halogen atoms and/or one to two of the following groups: $C_1$–$C_4$-alkoxy, $C_3$–$C_6$-alkenyloxy, $C_3$–$C_6$-alkynyloxy, $C_1$–$C_4$-alkylthio, $C_3$–$C_6$-alkenylthio, $C_3$–$C_6$-alkynylthio, $C_1$–$C_4$-haloalkoxy, $C_1$–$C_4$-alkylcarbonyl, $C_3$–$C_6$-alkenylcarbonyl, $C_3$–$C_6$- alkynylcarbonyl, $C_1$–$C_4$-alkoxycarbonyl, $C_3$–$C_6$-alkenyloxycarbonyl, $C_3$–$C_6$-alkynyloxycarbonyl, di-$C_1$–$C_4$-alkylamino, $C_3$–$C_8$-cycloalkyl, phenyl, or phenyl which is mono- or polysubstituted by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

phenyl, which can be substituted by one or more of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

$R^6$ and $R^7$ together are an unsubstituted or substituted $C_4$–$C_7$-alkylene chain which is closed to give a ring or together are an unsubstituted or substituted $C_3$–$C_6$-alkylene chain which is closed to give a ring and contains a heteroatom selected from the group consisting of oxygen, sulfur and nitrogen;

c) $R^1$ is additionally a group

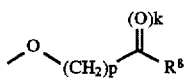

where $R^8$ is $C_1$–$C_4$-alkyl, phenyl, phenyl which is mono- or polysubstituted by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, or $C_1$–$C_4$-haloalkyl, $C_3$–$C_6$-alkenyl or $C_3$–$C_6$-alkynyl, p assumes the values 1, 2, 3 or 4 and k assumes the values 0, 1 or 2;

d) a radical $OR^9$, where $R^9$ is:
 I) a $C_3$–$C_8$-cycloalkyl group, which can carry one to three $C_1$–$C_4$-alkyl radicals;
 II) a $C_1$–$C_8$-alkyl group, which can carry one to five halogen atoms and/or one of the following radicals: $C_1$–$C_4$-alkoxy, $C_1$–$C_4$-alkylthio, cyano, $C_1$–$C_4$-alkylcarbonyl, $C_3$–$C_8$-cycloalkyl, $C_1$–$C_4$-alkoxycarbonyl, phenyl, or phenyl or phenoxy, which is mono- or polysubstituted by halogen, nitro, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;
 III) a $C_1$–$C_8$-alkyl group which can carry one to five halogen atoms and carries one of the following radicals: a 5-membered heteroaromatic, containing one to three nitrogen atoms, or a 5-membered heteroaromatic containing one nitrogen atom and an oxygen or sulfur atom, which can carry one to four halogen atoms and/or one to two of the following radicals: nitro, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;
 IV) a $C_2$–$C_6$-alkyl group, which in the 2-position carries one of the following radicals: $C_1$–$C_4$-alkoxyimino, $C_3$–$C_6$-alkenyloxyimino, $C_3$–$C_6$-haloalkenyloxyimino or benzyloxyimino;
 V) a $C_3$–$C_6$-alkenyl group or a $C_3$–$C_6$-alkynyl group, these groups in turn being able to carry one to five halogen atoms;
 VI) a phenyl radical, which can carry one to five halogen atoms and/or one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;
 VII) a 5-membered heteroaromatic linked via a nitrogen atom and containing one to three nitrogen atoms, which can carry one to two halogen atoms and/or one to two of the following radicals: nitro, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;
 VIII) $R^9$ is additionally a group $-N=CR^{10}OR^{11}$, where $R^{10}$ and $R^{11}$, which are identical or different, are:
  $C_1$–$Cl_2$-alkyl, $C_3$–$C_6$-alkenyl, $C_3$–$C_6$-alkynyl or $C_3$–$C_8$-cycloalkyl, these radicals being able to carry a $C_1$–$C_4$-alkoxy or $C_1$–$C_4$-alkylthio radical and/or a phenyl radical;
  phenyl, which can be substituted by one or more of the following radicals:
  halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;
  or $R^{10}$ and $R^{11}$ together form a $C_3$–$Cl_2$-alkylene chain, which can carry one to three $C_1$–$C_4$-alkyl groups;
e) or a radical $-NH-SO_2-R^{12}$, where $R^{12}$ is:
 $C_1$–$C_4$-alkyl, $C_3$–$C_6$-alkenyl, $C_3$–$C_6$-alkynyl or $C_3$–$C_8$-cycloalkyl, these radicals being able to carry a $C_1$–$C_4$-alkoxy or $C_1$–$C_4$-alkylthio radical and/or a phenyl radical;
 phenyl, which can be substituted by one or more of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio; and then reacting with a pyridine or triazine compound of the formula III where $R^{20}$ =halogen such as fluorine, chlorine, bromine, iodine, alkylsulfonyl, particularly methylsulfonyl or haloalkylsulfonyl, particularly trifluoromethylsulfonyl, in an inert solvent. Suitable radicals for $R^{20}$ are the radicals described above.

This reaction, which is the subject of the parallel German Application No. P 43 37 321.6, can be represented by the following reaction scheme:

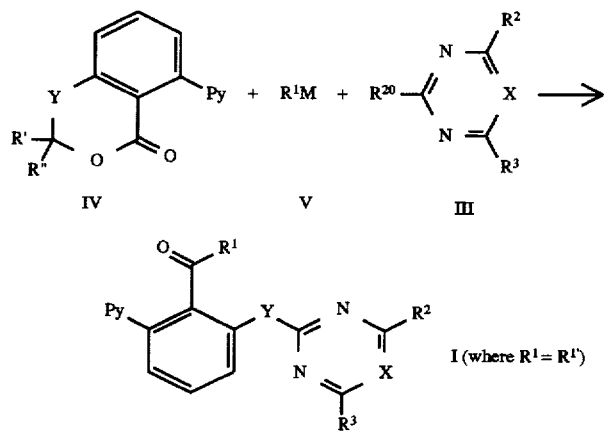

The reaction of the cyclic acetals IV with the salt V and the further reaction with the heterocycle of the formula III can be carried out in one reaction vessel directly to give the active compound I. In this case, the salt $R^1M$, which can also be prepared in situ from a compound $R^{1'}H$ and a base is added first. The heterocycle III is then added. III should advantageously only be added if the first step of the reaction, the addition of the salt V to the intermediate IV, is largely complete. This can last from a few minutes to several hours, the reaction temperature being from –40° C. to 200° C., usually from 0° C. to 130° C.

It is also possible to terminate the reaction after the first stage and to isolate the intermediate II (where $R^1 = R^{1'}$)

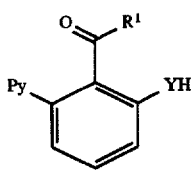

and to react further as described above.

In both cases the customary solvents are suitable, provided that they cannot be deprotonated themselves by the base or the salt $R^1M$ used and participate in the reaction. Polar solvents, eg. ethers such as diethyl ether, methyl tert-butyl ether, dimethoxyethane, tetrahydrofuran, dioxane, amides such as dimethylformamide, dimethylacetamide, N-methylpyrrolidone and dimethylpropyleneurea or dimethyl sulfoxide are particularly highly suitable. A phase transfer catalyst such as a crown ether or a quaternary ammonium salt can be added if this promotes the conversion.

The reaction temperature is from −40° to 200° C., preferably from 0° to 160° C. The reaction times are customarily from a few minutes to 50 hours, usually 0.5–10 hours.

In general, from 0.8 to 3, in particular from 0.9 to 1.5, mol equivalents of the compound V ($R^1M$) are employed per mole of starting substance IV. The amount of heterocycle III is likewise expediently from 0.8 to 3, in particular from 0.9 to 1.5, mol equivalents based on I.

The reaction can be carried out continuously or batchwise at atmospheric pressure, elevated pressure or reduced pressure.

The possibilities for working up are varied and depend in the individual case on the solubility of the product in the solvents used and on the miscibility of the solvents with water and the boiling points of the solvents. Both aqueous and non-aqueous work-ups are possible.

A suitable working-up method consists for example in mixing the reaction mixture, from which the solvent can also be partially or completely evaporated beforehand, with water and filtering off the product or extracting it with an organic solvent.

The starting substance IV can advantageously be prepared by reacting 6-hydroxybenzoic acids (for Y=O) or 6-mercaptobenzoic acids (for Y=S) with a compound O=CR'R" in the presence of an acidic catalyst:

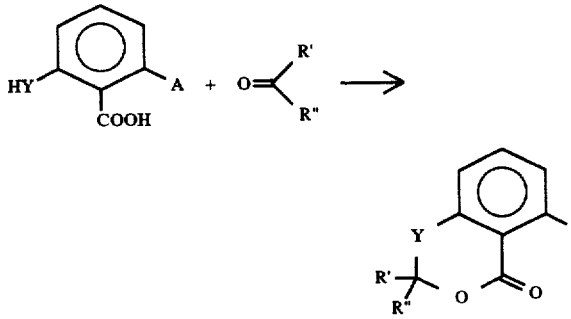

A is in this case a halogen atom, eg. chlorine, bromine or iodine, $C_1$–$C_4$-haloalkylsulfonyloxy, in particular trifluoromethylsulfonyloxy, $C_1$–$C_4$-alkylsulfonyloxy or fluorosulfonyloxy.

The starting substances are generally known or accessible in a generally known manner.

To bind the water formed in the reaction, a dehydrating agent can be added, such as eg. molecular sieve, acid anhydrides, such as trifluoroacetic anhydride, acetic anhydride, sodium sulfate or calcium chloride, if this promotes the conversion. A reactive acetal of the compound O=CR'R", such as eg. a dimethyl acetal, diethyl acetal, ethylene acetal or propylene acetal, is also suitable. Suitable catalysts are particularly acidic ion exchangers, protic acids such as eg. toluenesulfonic acid, sulfuric acid, phosphoric acid etc. or Lewis acids such as eg. aluminum chloride, titanium tetrachloride, zinc chloride, calcium chloride, magnesium chloride, tin chlorides etc. Often, the water formed or the alcohol formed from the acetal can be removed directly from the reaction mixture by distillation.

The further reaction to give the cyclic acetals IV is carried out using stannyl or boranyl compounds of the formula W-Py in the presence of a catalytically active palladium compound according to the following reaction scheme:

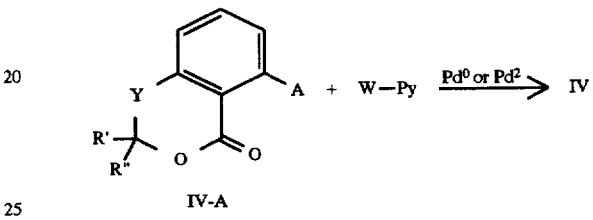

W is trialkylstannyl, eg. tri-$C_1$–$C_8$-alkylstannyl such as trimethylstannyl, triethylstannyl, tripropylstannyl, tributylstannyl, tripentylstannyl or trihexylstannyl, dihydroxyboranyl, dialkoxyboranyl, eg. di-$C_1$–$C_4$-alkoxyboranyl such as dimethoxyboranyl, diethoxyboranyl, dipropoxyboranyl, diisopropoxyboranyl or dibutoxyboranyl or isomers, or alkylenedioxyboranyl, eg. $C_1$–$C_4$-alkylenedioxyboranyl such as ethylenedioxyboranyl or 1,3-propylenedioxyboranyl. The boron or tin compounds used are either known or can be prepared in a similar way to known compounds.

A catalytically active palladium compound is employed in this novel process. Any desired palladium salts or complexes are suitable here which are at least partially soluble in the reaction mixture. The oxidation state of the palladium can be 0 or 2. In the case of the palladium salts, suitable counterions, inter alia, are the following: chloride, bromide, iodide, sulfate, acetate, trifluoroacetate, acetylacetonate or hexafluoro-2,4-pentane-dionate. Many different palladium complexes can be used. The precondition is only that the ligands on the palladium can be displaced from the substrate under the reaction conditions. Phosphine ligands such as eg. arylalkylphosphines such as, inter alia, methyldiphenylphosphine, isopropyldiphenylphosphine, triarylphosphines such as, inter alia, triphenylphosphine, tritolylphosphine, trixylylphosphine, trihetarylphosphines such as trifurylphosphine or dimeric phosphines are particularly suitable. Olefinic ligands such as, inter alia, dibenzylideneacetone or its salts, cycloocta-1,5-diene or amines such as trialkylamines (eg. triethylamine, tetramethylethylenediamine and N-methylmorpholine) or pyridine are also highly suitable.

The complex used can be employed directly in the reaction. The process can thus be carried out eg. using tetrakistriphenylphos-phinepalladium(0), bistriphenylphosphinepalladium dichloride, bistriphenylphosphinepalladium diacetate, a dibenzylideneacetone-palladium(0) complex, tetrakismethyldiphenylphosphinepalladium(0) or bis(1,2-diphenylphosphinoethane)palladium dichloride. A palladium salt and additionally a suitable ligand can also be used which then only form the catalytically active complex in situ. This procedure suggests itself eg. in the case of the abovementioned salts and phosphine ligands such as eg. trifurylphosphine or tritolylphosphine. Palladium complexes such as eg. tris(dibenzylideneacetone)dipalladium, bis(dibenzylideneacetone)palladium or 1,5-cyclooctadienepalladium dichloride can also be further activated by the addition of ligands such as eg. trifurylphosphine or tritolylphosphine.

Customarily, from 0.001 to 10 mol%, in particular from 0.005 to 5 mol%, of the palladium compound (salt or complex) are used, based on the compound W-Py. Higher amounts are possible but more uneconomical.

The amount of W-Py, based on the starting substance IV-A, is in general from 0.8 to 3, preferably from 0.95 to 1.5, mol equivalents.

All solvents which do not react themselves with the substrates used are suitable for the reaction. Polar solvents accelerate the reaction. Ethers such as diethyl ether, methyl tert-butyl ether, dimethoxyethane, tetrahydrofuran and dioxane, amides such as dimethylformamide, dimethylacetamide, N-methylpyrrolidone and dimethylpropyleneurea, or amines such as triethylamine are particularly suitable. The use of mixtures eg. of ethers with amides or mixtures of the abovementioned solvents with water or aliphatic alcohols is often advantageous. The addition of tetraalkylammonium halides or alkali metal halides such as eg. lithium chloride is often helpful and in particular to be recommended if A is a sulfonyloxy radical.

The reaction temperature is from $-20°$ to $200°$ C., preferably from $50°$ to $160°$ C. The reaction times are customarily from a few minutes to 50 hours, usually 0.5–10 hours. When using low-boiling solvents, it is sometimes useful to carry out the reaction under autogenous pressure in an autoclave.

If the compounds of the formula I prepared in the manner described are carboxylic acids (ie. if $R^1$ is hydroxyl), it is also possible to prepare eg. the carboxylic acid derivatives mentioned in claim 2 therefrom by first converting the carboxylic acid into an activated form such as a halide or imidazolide in a customary manner and then reacting this with the appropriate hydroxyl compound of the formula $R^1$-H. These two steps can also be simplified, for example, by allowing the carboxylic acid to act on the hydroxyl compound in the presence of a dehydrating agent such as eg. a carbodiimide or a suitable phosphonic anhydride.

Furthermore, carboxylic acids of the formula I (ie. where $R^1$ is hydroxyl) can also be reacted as follows to give many of the esters described: to do this the carboxylic acid is first converted into a salt, particularly an alkali metal salt, and this is then made to react, if appropriate in the presence of one of the bases mentioned further above, with an alkylating agent. The alkylating agent has the general formula $R^1$–$R^{21}$, the customary leaving groups such as, for example, chlorine, bromine, iodine, aryl- or alkylsulfonyl such as eg. toluenesulfonyl or methylsulfonyl being suitable for $R^{21}$. In general, the alkylating agents used are known or they can be prepared in a similar manner to the known compounds.

As herbicides, the compounds I or the compositions containing them and their environmentally tolerable salts eg. of alkali metals and alkaline earth metals can very effectively control broad-leaved weeds and grass weeds in crops such as wheat, rice, maize, soybean and cotton without damaging the crop plants, an effect which occurs especially even at low application rates.

The compounds I or the herbicidal compositions containing them can be applied by spraying, atomizing, dusting, broadcasting or watering, for example, in the form of directly sprayable aqueous solutions, powders, suspensions, even high-percentage aqueous, oily or other suspensions or dispersions, emulsions, oil dispersions, pastes, dusting compositions, broadcasting compositions or granules. The application forms depend on the intended uses; in each case they should if possible ensure the finest dispersion of the active compounds according to the invention.

The compounds I are generally suitable for preparing directly sprayable solutions, emulsions, pastes or oil dispersions. Suitable inert additives are mineral oil fractions of medium to high boiling point, such as kerosene or diesel oil, additionally coal tar oils and oils of vegetable or animal origin, aliphatic, cyclic and aromatic hydrocarbons, eg. paraffin, tetrahydronaphthalene, alkylated naphthalenes or their derivatives, alkylated benzenes or their derivatives, methanol, ethanol, propanol, butanol, cyclohexanol, cyclohexanone or strongly polar solvents, such as N-methylpyrrolidone or water.

Aqueous application forms can be prepared from emulsion concentrates, suspensions, pastes, wettable powders or water-dispersible granules by addition of water. To prepare emulsions, pastes or oil dispersions, the substrates as such or dissolved in an oil or solvent can be homogenized in water by means of wetting agents, adhesives, dispersants or emulsifiers. However, concentrates consisting of active substance, wetting agent, adhesive, dispersant or emulsifier and possibly solvent or oil can also be prepared, which are suitable for dilution with water.

Suitable surface-active substances are the alkali metal, alkaline earth metal and ammonium salts of aromatic sulfonic acids, eg. lignosulfonic, phenolsulfonic, naphthalenesulfonic and dibutylnaphthalenesulfonic acid, as well as of fatty acids, alkyl- and alkylarylsulfonates, alkyl-, lauryl ether and fatty alcohol sulfates, and also salts of sulfated hexa-, hepta- and octadecanols and of fatty alcohol glycol ethers, condensation products of sulfonated naphthalene and its derivatives with formaldehyde, condensation products of naphthalene or of naphthalenesulfonic acids with phenol and formaldehyde, polyoxyethylene octylphenol ether, ethoxylated isooctyl-, octyl- or nonylphenol, alkylphenol or tributylphenol polyglycol ethers, alkylaryl polyether alcohols, isotridecyl alcohol, fatty alcohol/ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Powder, broadcasting and dusting compositions can be prepared by mixing or joint grinding of the active substances with a solid carrier.

Granules, eg. coated, impregnated and homogeneous granules, can be prepared by binding the active compounds to solid carriers. Solid carriers are mineral earths such as silica gel, silicic acids, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products such as cereal flour, tree bark meal, wood meal and nutshell meal, cellulose powder or other solid carriers.

The formulations in general contain from 0.01 to 95% by weight, preferably from 0.5 to 90% by weight, of active compound. The active compounds are employed here in a purity of from 90% to 100%, preferably from 95% to 100% (by NMR spectrum).

The compounds I according to the invention can furthermore be formulated, for example, as follows:

I. 20 parts by weight of the compound No. 1.092 are dissolved in a mixture which consists of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid and 5 parts by weight of the addition product of 40 mol of ethylene oxide to 1 mol of castor oil. By pouring out the solution and finely dispersing it in 100,000 parts by weight of water, an aqueous dispersion is obtained which contains 0.02% by weight of the active compound.

II. 20 parts by weight of the compound No. 1.092 are dissolved in a mixture which consists of 40 parts by weight of cyclohexanone, 30 parts by weight of isobutanol, parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

III. 20 parts by weight of the active compound No. 1.092 are dissolved in a mixture which consists of 25 parts by weight of cyclohexanone, 65 parts by weight of a mineral oil fraction of boiling point 210° to 280° C. and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

IV. 20 parts by weight of the active compound No. 1.6 are well mixed with 3 parts by weight of the sodium salt of diisobutylnaphthalene a-sulfonic acid, 17 parts by weight of the sodium salt of a lignosulfonic acid from a sulfite waste liquor and 60 parts by weight of powdered silica gel and the mixture is ground in a hammer mill. By finely dispersing the mixture in 20,000 parts by weight of water, a spray mixture is obtained which contains 0.1% by weight of the active compound.

V. 3 parts by weight of the active compound No. 1.092 are mixed with 97 parts by weight of finely divided kaolin. In this way a dusting composition is obtained which contains 3% by weight of the active compound.

VI. 20 parts by weight of the active compound No. 1.092 are intimately mixed with 2 parts by weight of calcium salt of dodecylbenzenesulfonic acid, 8 parts by weight of fatty alcohol polyglycol ether, 2 parts by weight of sodium salt of a phenol/urea/formaldehyde condensate and 68 parts by weight of a paraffinic mineral oil. A stable oily dispersion is obtained.

The application of the herbicidal compositions or of the active compounds can be carried out pre-emergence or post-emergence. If the active compounds are less tolerable for certain crop plants, application techniques can be used in which the herbicidal compositions are sprayed with the aid of the spray equipment such that the leaves of the sensitive crop plants are not affected if possible, while the active compounds reach the leaves of undesired plants growing under them or the uncovered soil surface (post-directed, lay-by).

Depending on the target of control, time of year, target plants and stage of growth, the application rates of active compound are from 0.001 to 2.0, preferably from 0.01 to 1.0, kg/ha of active substance (a.s.).

In consideration of the variety of application methods, the compounds I according to the invention or compositions containing them can additionally be employed in a further number of crop plants for the elimination of undesired plants. Suitable crops are, for example, the following:

*Allium cepa, Ananas comosus, Arachis hypogaea, Asparagus officinalis, Beta vulgaris* spp. *altissima, Beta vulgaris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spp., *Manihot esculenta, Medicago sativa, Musa* spp., *Nicotiana tabacum* (*N. rustica*), *Olea europaea, Oryza sativa, Phaseolus lunatus, Phaseolus vulgaris, Picea abies, Pinus* spp., *Pisum sativum, Prunus avium, Prunus persica, Pyrus communis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera, Zea mays.*

The compounds of the formula I can furthermore affect the various stages of development of a plant and are therefore employed as growth regulators. The varied action of the plant growth regulators is especially dependent on the plant species and variety; on the time of application, relative to the stage of development of the plant, and on the time of year; on the type of application and application process (eg. seed-dressing, soil treatment, foliar application or stem injection in the case of trees); on climatic factors (eg. temperature, amount of precipitation, additionally length of day and light intensity); on the soil condition (including fertilization); on the formulation and application form of the active compound and on the concentrations of the active substance used.

A few, of the number of different possibilities for application of the plant growth regulators of the formula I according to the invention in plant cultivation, in agriculture and in horticulture are mentioned below:

A.

The vegetative growth of the plants can be severely inhibited by the compounds which can be used according to the invention, which is manifested in particular in a reduction in the longitudinal growth. The treated plants accordingly exhibit stocky growth; additionally darker leaf coloration is to be observed.

A decreased intensity in the growth of grasses on roadsides, hedgerows, canal banks and on plots of grass such as parks, sports grounds and orchards, ornamental lawns and airfields proves to be advantageous in practice, so that the labor- and cost-intensive mowing can be reduced.

The increase in the resistance of crops susceptible to lodging, such as cereals, maize, sunflowers and soybeans, is also of economic interest. The culm shortening and culm strengthening caused in this case decrease or eliminate the danger of lodging (of being bent over) of plants under unfavorable weather conditions before harvesting.

The application of growth regulators for inhibiting the longitudinal growth and for temporally altering the course of ripening in cotton is also important. Completely mechanized harvesting of this important crop plant is thus made possible.

In the case of fruit and other trees, pruning costs can be saved using the growth regulators. In addition, the alternation of fruit trees can be broken by means of growth regulators.

The lateral branching of the plants can also be increased or inhibited by application of growth regulators. There is interest in this if, eg. in the case of tobacco plants, the formation of side shoots (suckers) is to be inhibited in favor of leaf growth.

In the case of winter rape, for example, the frost resistance can also be considerably increased using growth regulators. In this case, on the one hand, the longitudinal growth and the development of an excessively luxuriant (and thereby particularly frost-susceptible) herbage or biomass are inhibited. On the other hand, after sowing and before the winter frosts set in the young rape plants are held back in the vegetative development stage despite favorable growth conditions. As a result, the frost danger to those plants which are prone to premature degeneration of the inhibition of flowering and to transition into the generative phase is eliminated. Even in other crops, eg. winter cereals, it is advantageous if the populations are indeed well tillered by treatment with compounds according to the invention in the autumn, but are not too luxuriant when going into the winter. As a result, the increased frost sensitivity and, because of the relatively low herbage or biomass, attack by various diseases (eg. fungal disease) can be prevented. The inhibition of the vegetative growth additionally makes possible a more compact planting of the soil with many crop plants, so that an additional yield can be achieved, based on the soil area.

B.

Additional yields both of parts of plants and of plant constituents can be achieved using the growth regulators. Thus it is possible, for example, to induce the growth of greater amounts of buds, flowers, leaves, fruit, seeds, roots and tubers, to increase the content of sugar in sugar beet, sugar cane and citrus fruits, to raise the protein content in cereals or soybeans or to stimulate rubber trees to an increased flow of latex.

In this case, the compounds of the formula I can cause increases in yield by intervention in the plant metabolism or by promotion or inhibition of vegetative and/or of generative growth.

C.

Finally, both reduction or prolongation of the development stages and acceleration or retardation of the ripening of the harvested parts of plants before or after harvesting can be achieved using plant growth regulators.

Of economic interest, for example, is the facilitation of harvesting, which is made possible by the temporally concentrated fall or decrease in the adhesiveness to the tree in the case of citrus fruits, olives or in the case of other species and varieties of pomaceous fruit, stone fruit and hard-shell dry fruit. The same mechanism, that is the promotion of the formation of abscission tissue between the fruit or leaf and shoot part of the plant, is also essential for a well-controllable defoliation of productive plants such as, for example, cotton.

D.

The intensity of irrigation can be reduced by the use of the substances according to the invention and thus a more economical management can be carried out. Under the influence of growth regulators, a better utilization of the water present, for example, occurs because, inter alia, the opening width of the stomata is reduced, a thicker epidermis and cuticle are formed, the root penetration of the soil is improved and the microclimate in the plant population is favorably influenced by a more compact growth.

The compounds I are particularly suitable for culm shortening of crop plants such as barley, rape and wheat.

The growth regulators of the formula I to be used according to the invention can be supplied to the crop plants both from seeds (as seed-dressing agents) and via the soil, ie. by the roots and, particularly preferably, by spraying over the leaf. The compositions are prepared here in a similar manner to the herbicides (see above).

As a result of the high plant compatibility, the application rate of active compound is not critical. The optimum application rate varies depending on the target of control, time of year, target plants and stages of growth.

To widen the spectrum of action and to achieve synergistic effects, the pyridylsalicylaldehyde and -salicylic acid derivatives I can be mixed with numerous representatives of other herbicidal or growth-regulating active compound groups and applied together. For example, suitable herbicidal mixture components are diazines, 4H-3,1-benzoxazine derivatives, benzothia-diazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which carry eg. a carboxyl or carbimino group in the 2-position, quinolinecarboxylic acid derivatives, imidazolines, sulfonamides, sulfonylureas, aryloxy- and heteroaryloxyphenoxypropionic acids and their salts, esters and amides and others. Suitable growth regulators are in particular chlormequat chloride, ethylene and mepiquat chloride.

It may additionally be useful to apply the compounds I on their own or together in combination with other herbicides or growth regulators and additionally mixed with further crop protection agents, for example with agents for controlling pests or phytopathogenic fungi or bacteria. Additionally of interest is the miscibility with mineral salt solutions which are employed for the elimination of nutritional and trace element deficiencies. Non-phytotoxic oils and oil concentrates can also be added.

SYNTHESIS EXAMPLES

Example 1

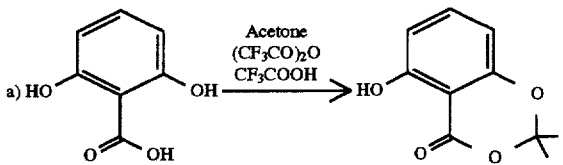

5-Hydroxy-2,2-dimethyl-4H-(1,3)benzodioxin-4-one 100 g (0.66 mol) of 2,6-dihydroxybenzoic acid are initially introduced into 800 ml of trifluoroacetic acid, and 100 ml of acetone and 216 g (1.98 mol) of trifluoroacetic anhydride are added. The mixture is refluxed for about 2 h, and 50 ml of acetone per hour are then added dropwise under reflux (total reaction time 7.5 h, total acetone addition 375 ml). The reaction mixture is concentrated under reduced pressure at about 55° C., made up three times with toluene and concentrated again, and the residue is finally dried at 45° C. on an oil pump.

The oily product is taken up in 2 l of methyl tert-butyl ether, and the solution is treated with 2 l of water and 2 l of saturated NaHCO$_3$ solution and stirred for 1.5 h. The aqueous phase is separated off and extracted with methyl tert-butyl ether, and the combined organic phases are washed with sodium chloride solution, dried over sodium sulfate and concentrated. The residue is stirred with 200 ml of n-pentane, filtered off with suction and dried. Yield: 115 g (90%). M.p. 60°–62° C.

b)

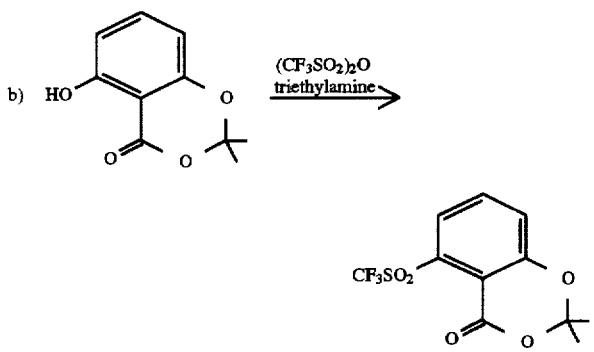

2.2-Dimethyl-5-trifluoromethylsulfonyloxy-4H-(1,3) benzodioxin-4-one:

80 g (0.41 mol) of 5-hydroxy-2,2-dimethyl-4H-(1,3) benzodioxin-4-one are dissolved in 1.5 l of methylene chloride. 129 g (1.28 mol) of triethylamine are added at 0C and 314 g (1.11 mol) of trifluoromethylsulfonic anhydride are then added dropwise in the course of 2 h. The mixture is allowed to warm to 10° C., is subsequently stirred at this temperature for 10 min and is then added with stirring to 1.5 l of water at 0° C. The organic phase is separated off, the aqueous phase is extracted with methylene chloride, and the combined organic phases are washed with water and once with saturated sodium chloride solution, dried over sodium sulfate and concentrated. The residue is stirred with 200 ml of n-pentane, filtered off, subsequently washed with n-pentane and dried at 40° C. on an oil pump. Yield: 118 g (88%). Melting point: 115° C.

c)

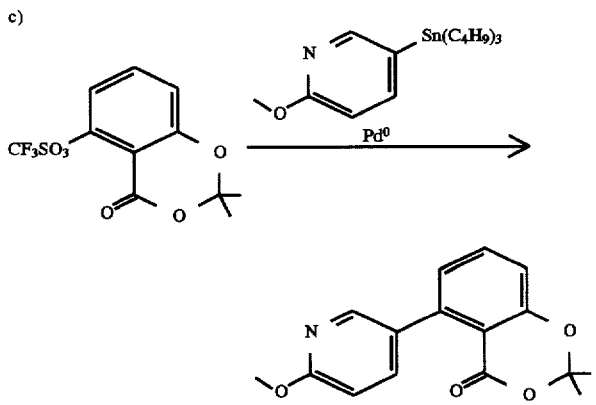

2.2-Dimethyl-5-(2-methoxypyridin-5-yl)-4H-(1,3) benzodioxin-4-one 8.7 g of 2,2-dimethyl-5-trifluoromethylsulfonyloxy-4H-(1,3)benzo-dioxin-4-one, 23.2 g of 2-methoxy-5-tributylstannylpyridine, 3.4 g of lithium chloride, 0.6 g of tetrakistriphenylphosphine-palladium⁰ and 70 mg of 2,6-di-t-butyl-4-methylphenol are dissolved in 150 ml of dioxane and the mixture is stirred for 3 h at 140° C. in an autoclave. It is then concentrated under reduced pressure, the residue is stirred with 200 ml of n-pentane and filtered on a little silica gel 60, the latter is subsequently 40 washed with n-pentane and the product is eluted using ethyl acetate. After concentration, 10.3 g of m.p. 160° C. remain.

d)

2-(4,6-Dimethoxypyrimidin-2-yloxy)-6-(2-methoxypyridin-5-yl)-benzoic acid acetone oxime ester (Compound 2.008)

0.67 g of acetone oxime, dissolved in 30 ml of toluene, is treated with 1.66 g of a 30% strength sodium methoxide solution in methanol and the mixture is concentrated under reduced pressure. 35 ml of dimethylformamide and then 2.50 g of 2,2-dimethyl-5-(2-methoxypyridin-5-yl)-4H-(1,3) benzodioxin-4-one are added, the mixture is stirred for 15 min at room temperature and 1.90 g of 4,6-dimethoxy-2-methylsulfonylpyrimidine are finally added. The reaction mixture is subsequently stirred for several hours, poured into 300 ml of water and extracted with methyl t-butyl ether, and the organic phase is washed thoroughly with water and saturated sodium chloride solution, dried over sodium sulfate and concentrated under reduced pressure. The crude product is purified by chromatography on silica gel 60 using n-hexane/ethyl acetate. ¹H-NMR (CDC₁₃): see Table 2.

Example 2 a)

2,2-Dimethyl-5-(6-methoxypyridin-2-yl)-4H-(1,3) benzodioxin-4-one 10.9 g of 2,2-dimethyl-5-trifluoromethylsulfonyloxy-4H-(1,3)-benzodioxin-4-one, 16.0 g of 6-methoxy-2-tributylstannylpyridine, 4.25 g of lithium chloride, 0.78 g of tetrakistriphenylphosphine-palladium⁰ and 40 mg of 2.6-di-t-butyl-4-methylphenol are dissolved in 120 ml of dioxane and the mixture is stirred for 4 h at 140° C. in an autoclave. It is concentrated under reduced pressure and the product is chromatographed on silica gel 60 using ethyl acetate/ toluene. 9.1 g (95%) of a solid of m.p. 130–132° C. are obtained.

b)

Benzyl 2-(4,6-dimethoxypyrimidin-2-yloxy)-6-(6-methoxypyri-din-2-yl)benzoate (Compound 1.012)

1.36 g of benzyl alcohol dissolved in 50 ml of dimethylformamide are treated with 380 mg of sodium hydride (80% strength in liquid paraffin) and the mixture is subsequently stirred at room temperature for about 1 h. 3.0 g of 2,2-dimethyl-5-(6-methoxypyridin-2-yl)-4H-(1,3)benzodioxin-4-one are added, the mixture is stirred at room temperature for 3 h and 2.65 g of 4,6-dimethoxy-2-methylsulfonylpyrimidine are finally added. The mixture is stirred at room temperature for 2 h, at 80° C. for 1.5 h and at 115° C. for 3 h, poured into ice-water containing phosphoric acid and extracted with ethyl acetate, and the organic phase is washed with water, dried over sodium sulfate and concentrated under reduced pressure. The crude product is purified by chromatography on silica gel 60 using cyclohexane/toluene/ethyl acetate. ¹H-NMR (CDCl₃): see Table 1.

Example 3

2-(4,6-Dimethoxypyrimidin-2-yloxy)-6-(6-methoxypyridin-2-yl)-benzoic acid (Compound 1.004)

1.57 g of benzyl 2-(4,6-dimethoxypyrimidin-2-yloxy)-6-(6-methoxypyridin-2-yl)benzoate and 560 mg of palladium on active carbon (10%) in 100 ml of diethyl ether are hydrogenated at room temperature for 10 h at a hydrogen pressure of 50 bar. A further 300 mg of catalyst are then added and the mixture is hydrogenated at room temperature for another 10 h at a hydrogen pressure of 50 bar. The mixture is filtered through Celite® (Aldrich) and concentrated under reduced pressure. Yield: 0.99 g of a solid of m.p. 158°–160° C.

Particularly preferred compounds of the formula I which can be prepared as described in the previous examples are compiled in the following Tables 1 to 6.

TABLE 1

| No. | R¹ | R³ | X | R¹⁴ | R¹⁵ | R¹⁶ | R¹⁷ | Phys. data (m.p. [°C.]¹H-NMR*, selected signals) |
|---|---|---|---|---|---|---|---|---|
| 1.001 | OH | OCH₃ | CH | 3-OCH₃ | H | H | H | |
| 1.002 | OH | OCH₃ | CH | 4-OCH₃ | H | H | H | |
| 1.003 | OH | OCH₃ | CH | 5-OCH₃ | H | H | H | |
| 1.004 | OH | OCH₃ | CH | 6-OCH₃ | H | H | H | 158–160 |
| 1.005 | 2-Propaniminoxy | OCH₃ | CH | 3-OCH₃ | H | H | H | |
| 1.006 | 2-Propaniminoxy | OCH₃ | CH | 4-OCH₃ | H | H | H | |
| 1.007 | 2-Propaniminoxy | OCH₃ | CH | 5-OCH₃ | H | H | H | |
| 1.008 | 2-Propaniminoxy | OCH₃ | CH | 6-OCH₃ | H | H | H | 140–141 |
| 1.009 | Benzyloxy | OCH₃ | CH | 3-OCH₃ | H | H | H | |
| 1.010 | Benzyloxy | OCH₃ | CH | 4-OCH₃ | H | H | H | |
| 1.011 | Benzyloxy | OCH₃ | CH | 5-OCH₃ | H | H | H | |
| 1.012 | Benzyloxy | OCH₃ | CH | 6-OCH₃ | H | H | H | δ=3.80(s); 3.89(s); 5.02(s); 5.72(s); 6.67(d); 6.7–7.7(m). |
| 1.013 | OH | OCH₃ | CH | 3-OC₂H₅ | H | H | H | |
| 1.014 | OH | OCH₃ | CH | 4-OC₂H₅ | H | H | H | |
| 1.015 | OH | OCH₃ | CH | 5-OC₂H₅ | H | H | H | |
| 1.016 | OH | OCH₃ | CH | 6-OC₂H₅ | H | H | H | 157–158 |
| 1.017 | 2-Propaniminoxy | OCH₃ | CH | 3-OC₂H₅ | H | H | H | |
| 1.018 | 2-Propaniminoxy | OCH₃ | CH | 4-OC₂H₅ | H | H | H | |
| 1.019 | 2-Propaniminoxy | OCH₃ | CH | 5-OC₂H₅ | H | H | H | |
| 1.020 | 2-Propaniminoxy | OCH₃ | CH | 6-OC₂H₅ | H | H | H | δ=1.33(t); 1.58(s); 1.95(s); 3.81(s); 4.35(q); 5.75(s); 6.67(d); 7.2–7.7(m). |
| 1.021 | Benzyloxy | OCH₃ | CH | 3-OC₂H₅ | H | H | H | |
| 1.022 | Benzyloxy | OCH₃ | CH | 4-OC₂H₅ | H | H | H | |
| 1.023 | Benzyloxy | OCH₃ | CH | 5-OC₂H₅ | H | H | H | |
| 1.024 | Benzyloxy | OCH₃ | CH | 6-OC₂H₅ | H | H | H | δ=1.33(t, 3H); 3.79(s, 6H), 4.32(q); 5.02(s); 5.72(s); 6.67(d); 6.9–7.7(m) |
| 1.025 | OH | OCH₃ | CH | 3-O-i-C₃H₇ | H | H | H | |
| 1.026 | OH | OCH₃ | CH | 4-O-i-C₃H₇ | H | H | H | |
| 1.027 | OH | OCH₃ | CH | 5-O-i-C₃H₇ | H | H | H | |
| 1.028 | OH | OCH₃ | CH | 6-O-i-C₃H₇ | H | H | H | |
| 1.029 | 2-Propaniminoxy | OCH₃ | CH | 3-O-i-C₃H₇ | H | H | H | |
| 1.030 | 2-Propaniminoxy | OCH₃ | CH | 4-O-i-C₃H₇ | H | H | H | |
| 1.031 | 2-Propaniminoxy | OCH₃ | CH | 5-O-i-C₃H₇ | H | H | H | |
| 1.032 | 2-Propaniminoxy | OCH₃ | CH | 6-O-i-C₃H₇ | H | H | H | |
| 1.033 | Benzyloxy | OCH₃ | CH | 3-O-i-C₃H₇ | H | H | H | |
| 1.034 | Benzyloxy | OCH₃ | CH | 4-O-i-C₃H₇ | H | H | H | |
| 1.035 | Benzyloxy | OCH₃ | CH | 5-O-i-C₃H₇ | H | H | H | |
| 1.036 | Benzyloxy | OCH₃ | CH | 6-O-i-C₃H₇ | H | H | H | |
| 1.037 | OH | OCH₃ | CH | 3-O-i-C₃H₇ | H | H | H | |
| 1.038 | OH | OCH₃ | CH | 4-O-i-C₃H₇ | H | H | H | |
| 1.039 | OH | OCH₃ | CH | 5-O-i-C₃H₇ | H | H | H | |
| 1.040 | OH | OCH₃ | CH | 6-O-i-C₃H₇ | H | H | H | 164–165 |
| 1.041 | 2-Propaniminoxy | OCH₃ | CH | 3-O-i-C₃H₇ | H | H | H | |
| 1.042 | 2-Propaniminoxy | OCH₃ | CH | 4-O-i-C₃H₇ | H | H | H | |
| 1.043 | 2-Propaniminoxy | OCH₃ | CH | 5-O-i-C₃H₇ | H | H | H | |
| 1.044 | 2-Propaniminoxy | OCH₃ | CH | 6-O-i-C₃H₇ | H | H | H | δ=1.28(d); 1.52(s); 1.93(s); 3.82(s); 5.38(m); 5.76(s); 6.63(d); 7.2–7.7(m). |
| 1.045 | Benzyloxy | OCH₃ | CH | 3-O-i-C₃H₇ | H | H | H | |
| 1.046 | Benzyloxy | OCH₃ | CH | 4-O-i-C₃H₇ | H | H | H | |
| 1.047 | Benzyloxy | OCH₃ | CH | 5-O-i-C₃H₇ | H | H | H | |
| 1.048 | Benzyloxy | OCH₃ | CH | 6-O-i-C₃H₇ | H | H | H | δ=1.30(d); 3.78(s); 5.00(s); 5.35(m); 5.75(s); 6.62(d); 6.9–7.7(m). |
| 1.049 | OH | OCH₃ | CH | 3-SCH₃ | H | H | H | |
| 1.050 | OH | OCH₃ | CH | 4-SCH₃ | H | H | H | |

TABLE 1-continued

| No. | R¹ | R³ | X | R¹⁴ | R¹⁵ | R¹⁶ | R¹⁷ | Phys. data (m.p. [°C.]¹H-NMR*, selected signals) |
|---|---|---|---|---|---|---|---|---|
| 1.051 | OH | OCH₃ | CH | 5-SCH₃ | H | H | H | |
| 1.052 | OH | OCH₃ | CH | 6-SCH₃ | H | H | H | |
| 1.053 | 2-Propaniminoxy | OCH₃ | CH | 3-SCH₃ | H | H | H | |
| 1.054 | 2-Propaniminoxy | OCH₃ | CH | 4-SCH₃ | H | H | H | |
| 1.055 | 2-Propaniminoxy | OCH₃ | CH | 5-SCH₃ | H | H | H | |
| 1.056 | 2-Propaniminoxy | OCH₃ | CH | 6-SCH₃ | H | H | H | 140–141 |
| 1.057 | Benzyloxy | OCH₃ | CH | 3-SCH₃ | H | H | H | |
| 1.058 | Benzyloxy | OCH₃ | CH | 4-SCH₃ | H | H | H | |
| 1.059 | Benzyloxy | OCH₃ | CH | 5-SCH₃ | H | H | H | |
| 1.060 | Benzyloxy | OCH₃ | CH | 6-SCH₃ | H | H | H | 121–122 |
| 1.061 | OH | OCH₃ | CH | 3-SC₂H₅ | H | H | H | |
| 1.062 | OH | OCH₃ | CH | 4-SC₂H₅ | H | H | H | |
| 1.063 | OH | OCH₃ | CH | 5-SC₂H₅ | H | H | H | |
| 1.064 | OH | OCH₃ | CH | 6-SC₂H₅ | H | H | H | |
| 1.065 | 2-Propaniminoxy | OCH₃ | CH | 3-SC₂H₅ | H | H | H | |
| 1.066 | 2-Propaniminoxy | OCH₃ | CH | 4-SC₂H₅ | H | H | H | |
| 1.067 | 2-Propaniminoxy | OCH₃ | CH | 5-SC₂H₅ | H | H | H | |
| 1.068 | 2-Propaniminoxy | OCH₃ | CH | 6-SC₂H₅ | H | H | H | |
| 1.069 | Benzyloxy | OCH₃ | CH | 3-SC₂H₅ | H | H | H | |
| 1.070 | Benzyloxy | OCH₃ | CH | 4-SC₂H₅ | H | H | H | |
| 1.071 | Benzyloxy | OCH₃ | CH | 5-SC₂H₅ | H | H | H | |
| 1.072 | Benzyloxy | OCH₃ | CH | 6-SC₂H₅ | H | H | H | |
| 1.073 | OH | OCH₃ | CH | 3-S-n-C₃H₇ | H | H | H | |
| 1.074 | OH | OCH₃ | CH | 4-S-n-C₃H₇ | H | H | H | |
| 1.075 | OH | OCH₃ | CH | 5-S-n-C₃H₇ | H | H | H | |
| 1.076 | OH | OCH₃ | CH | 6-S-n-C₃H₇ | H | H | H | |
| 1.077 | 2-Propaniminoxy | OCH₃ | CH | 3-S-n-C₃H₇ | H | H | H | |
| 1.078 | 2-Propaniminoxy | OCH₃ | CH | 4-S-n-C₃H₇ | H | H | H | |
| 1.079 | 2-Propaniminoxy | OCH₃ | CH | 5-S-n-C₃H₇ | H | H | H | |
| 1.080 | 2-Propaniminoxy | OCH₃ | CH | 6-S-n-C₃H₇ | H | H | H | |
| 1.081 | Benzyloxy | OCH₃ | CH | 3-S-n-C₃H₇ | H | H | H | |
| 1.082 | Benzyloxy | OCH₃ | CH | 4-S-n-C₃H₇ | H | H | H | |
| 1.083 | Benzyloxy | OCH₃ | CH | 5-S-n-C₃H₇ | H | H | H | |
| 1.084 | Benzyloxy | OCH₃ | CH | 6-S-n-C₃H₇ | H | H | H | |
| 1.085 | OH | OCH₃ | CH | 3-S-i-C₃H₇ | H | H | H | |
| 1.086 | OH | OCH₃ | CH | 4-S-i-C₃H₇ | H | H | H | |
| 1.087 | OH | OCH₃ | CH | 5-S-i-C₃H₇ | H | H | H | |
| 1.088 | OH | OCH₃ | CH | 6-S-i-C₃H₇ | H | H | H | |
| 1.089 | 2-Propaniminoxy | OCH₃ | CH | 3-S-i-C₃H₇ | H | H | H | |
| 1.090 | 2-Propaniminoxy | OCH₃ | CH | 4-S-i-C₃H₇ | H | H | H | |
| 1.091 | 2-Propaniminoxy | OCH₃ | CH | 5-S-i-C₃H₇ | H | H | H | |
| 1.092 | 2-Propaniminoxy | OCH₃ | CH | 6-S-i-C₃H₇ | H | H | H | 103–105 |
| 1.093 | Benzyloxy | OCH₃ | CH | 3-S-i-C₃H₇ | H | H | H | |
| 1.094 | Benzyloxy | OCH₃ | CH | 4-S-i-C₃H₇ | H | H | H | |
| 1.095 | Benzyloxy | OCH₃ | CH | 5-S-i-C₃H₇ | H | H | H | |
| 1.096 | Benzyloxy | OCH₃ | CH | 6-S-i-C₃H₇ | H | H | H | δ=1.33(d); 3.75(s); 4.07(m); 4.99(s); 5.72(s); 6.9–7.6(m). |
| 1.097 | OH | OCH₃ | CH | 6-OCH₂CF₃ | H | H | H | 148–149 |
| 1.098 | 2-Propaniminoxy | OCH₃ | CH | 6-OCH₂CF₃ | H | H | H | 97–98 |
| 1.099 | Benzyloxy | OCH₃ | CH | 6-OCH₂CF₃ | H | H | H | 107–108 |
| 1.100 | OH | OCH₃ | CH | 6-OCH₂CH₂OCH₃ | H | H | H | 134–135 |
| 1.101 | 2-Propaniminoxy | OCH₃ | CH | 6-OCH₂CH₂OCH₃ | H | H | H | 106–107 |
| 1.102 | Benzyloxy | OCH₃ | CH | 6-OCH₂CH₂OCH₃ | H | H | H | δ=3.40(s), 3.66(mc), 3.78(s), 4.44(mc), 5.00(s), 5.73(s), 6.76(d), 6.9–7.7(m) |
| 1.103 | OH | OCH₃ | CH | 6-OCH₂CH₂N(CH₃)₂ | H | H | H | 126–128 |
| 1.104 | 2-Propaniminoxy | OCH₃ | CH | 6-OCH₂CH₂N(CH₃)₂ | H | H | H | δ=1.55(s), 1.92(s), 2.50(s), 2.94(mc), 3.80(s), 4.52(mc), 5.72(s), 6.75(d); 7.20–7.70(m) |
| 1.105 | Benzyloxy | OCH₃ | CH | 6-OCH₂CH₂N(CH₃)₂ | H | H | H | δ=2.28(s), 2.62(mc), |

TABLE 1-continued

| No. | R¹ | R³ | X | R¹⁴ | R¹⁵ | R¹⁶ | R¹⁷ | Phys. data (m.p. [°C.]¹H-NMR*, selected signals) |
|---|---|---|---|---|---|---|---|---|
| | | | | | | | | 3.78(s), 4.38(mc), 5.01(s), 5.72(s), 6.75(d), 6.9–7.7(m) |
| 1.106 | OH | OCH₃ | CH | 6-ON(CH₃)₂ | H | H | H | |
| 1.107 | 2-Propaniminoxy | OCH₃ | CH | 6-ON(CH₃)₂ | H | H | H | |
| 1.108 | Benzyloxy | OCH₃ | CH | 6-ON(CH₃)₂ | H | H | H | |
| 1.109 | OCH₂CF₃ | OCH₃ | CH | 3-OCH₃ | H | H | H | |
| 1.110 | OCH₂CF₃ | OCH₃ | CH | 4-OCH₃ | H | H | H | |
| 1.111 | OCH₂CF₃ | OCH₃ | CH | 5-OCH₃ | H | H | H | |
| 1.112 | OCH₂CF₃ | OCH₃ | CH | 6-OCH₃ | H | H | H | |
| 1.113 | Propargyloxy | OCH₃ | CH | 3-OCH₃ | H | H | H | |
| 1.114 | Propargyloxy | OCH₃ | CH | 4-OCH₃ | H | H | H | |
| 1.115 | Propargyloxy | OCH₃ | CH | 5-OCH₃ | H | H | H | |
| 1.116 | Propargyloxy | OCH₃ | CH | 6-OCH₃ | H | H | H | |
| 1.117 | Allyloxy | OCH₃ | CH | 3-OCH₃ | H | H | H | |
| 1.118 | Allyloxy | OCH₃ | CH | 4-OCH₃ | H | H | H | |
| 1.119 | Allyloxy | OCH₃ | CH | 5-OCH₃ | H | H | H | |
| 1.120 | Allyloxy | OCH₃ | CH | 6-OCH₃ | H | H | H | |
| 1.121 | OH | OCH₂CH₂ | | 3-OCH₃ | H | H | H | |
| 1.122 | OH | OCH₂CH₂ | | 4-OCH₃ | H | H | H | |
| 1.123 | OH | OCH₂CH₂ | | 5-OCH₃ | H | H | H | |
| 1.124 | OH | OCH₂CH₂ | | 6-OCH₃ | H | H | H | |
| 1.125 | OH | OCH₃ | CF | 3-OCH₃ | H | H | H | |
| 1.126 | OH | OCH₃ | CF | 4-OCH₃ | H | H | H | |
| 1.127 | OH | OCH₃ | CF | 5-OCH₃ | H | H | H | |
| 1.128 | OH | OCH₃ | CF | 6-OCH₃ | H | H | H | |
| 1.129 | OH | OCH₃ | CH | 3-SCH₃ | 4-(CH₃) | H | H | |
| 1.130 | OH | OCH₃ | CH | 3-SCH₃ | 5-(CH₃) | H | H | |
| 1.131 | OH | OCH₃ | CH | 3-SCH₃ | 6-(CH₃) | H | H | |
| 1.132 | OH | OCH₃ | CH | 4-SCH₃ | 3-(CH₃) | H | H | |
| 1.133 | OH | OCH₃ | CH | 4-SCH₃ | 5-(CH₃) | H | H | |
| 1.134 | OH | OCH₃ | CH | 4-SCH₃ | 6-CH₃ | H | H | |
| 1.135 | OH | OCH₃ | CH | 5-SCH₃ | 4-CH₃ | H | H | |
| 1.136 | OH | OCH₃ | CH | 5-SCH₃ | 3-CH₃ | H | H | |
| 1.137 | OH | OCH₃ | CH | 5-SCH₃ | 6-CH₃ | H | H | |
| 1.138 | OH | OCH₃ | CH | 6-SCH₃ | 4-CH₃ | H | H | |
| 1.139 | OH | OCH₃ | CH | 6-SCH₃ | 5-CH₃ | H | H | |
| 1.140 | OH | OCH₃ | CH | 6-SCH₃ | 3-CH₃ | H | H | |
| 1.141 | OH | OCH₃ | CH | 3-OCH₃ | 4-CH₃ | H | H | |
| 1.142 | OH | OCH₃ | CH | 3-OCH₃ | 5-CH₃ | H | H | |
| 1.143 | OH | OCH₃ | CH | 3-OCH₃ | 6-CH₃ | H | H | |
| 1.144 | OH | OCH₃ | CH | 4-OCH₃ | 3-CH₃ | H | H | |
| 1.145 | OH | OCH₃ | CH | 4-OCH₃ | 5-CH₃ | H | H | |
| 1.146 | OH | OCH₃ | CH | 4-OCH₃ | 6-CH₃ | H | H | |
| 1.147 | OH | OCH₃ | CH | 5-OCH₃ | 4-CH₃ | H | H | |
| 1.148 | OH | OCH₃ | CH | 5-OCH₃ | 3-CH₃ | H | H | |
| 1.149 | OH | OCH₃ | CH | 5-OCH₃ | 6-CH₃ | H | H | |
| 1.150 | OH | OCH₃ | CH | 6-OCH₃ | 4-CH₃ | H | H | |
| 1.151 | OH | OCH₃ | CH | 6-OCH₃ | 5-CH₃ | H | H | |
| 1.152 | OH | OCH₃ | CH | 6-OCH₃ | 3-CH₃ | H | H | |
| 1.153 | OH | OCH₃ | CH | 6-OCH₃ | 3-F | H | H | |
| 1.154 | OH | OCH₃ | CH | 6-OCH₃ | 3-Cl | H | H | |
| 1.155 | OH | OCH₃ | CH | 3-OCH₃ | 6-OCH₃ | H | H | |
| 1.156 | OH | OCH₃ | CH | 4-OCH₃ | 6-OCH₃ | H | H | |
| 1.157 | OH | OCH₃ | CH | 3-OCH₃ | 6-F | H | H | |
| 1.158 | OH | OCH₃ | CH | 4-OC₂H₅ | 6-OC₂H₅ | H | H | |
| 1.159 | 2-Propaniminoxy | OCH₃ | CH | 6-O-n-C₃H₇ | H | H | H | 93–95 |
| 1.160 | Benzyloxy | OCH₃ | CH | 6-O-n-C₃H₇ | H | H | H | 91–92 |
| 1.161 | OH | OCH₃ | N | 6-OCH₃ | H | H | H | 144–146 |
| 1.162 | 2-Propaniminoxy | OCH₃ | CH | 6-O-n-C₃H₇ | H | H | H | 141–143 |
| 1.163 | 2-(Ethoxyimino)-propoxy | OCH₃ | CH | 6-O-C₂H₅ | H | H | H | δ=1.18(t), 1.29(t), 1.45(s), 3.77(s), 4.00(q), 4.22(q) 4.44(s), 6.03(s), |

TABLE 1-continued

| No. | R¹ | R³ | X | R¹⁴ | R¹⁵ | R¹⁶ | R¹⁷ | Phys. data (m.p. [°C.]¹H-NMR*, selected signals) |
|---|---|---|---|---|---|---|---|---|
| | | | | | | | | 6.79(d), 7.3–7.9(m) |
| 1.164 | OH | OCH₃ | CH | 6-N(CH₃)₂ | H | H | H | |
| 1.165 | OH | OCH₃ | CH | 5-N(CH₃)₂ | H | H | H | |
| 1.166 | OH | OCH₃ | CH | 4-N(CH₃)₂ | H | H | H | |
| 1.167 | OH | OCH₃ | CH | 3-N(CH₃)₂ | H | H | H | |
| 1.168 | 2-Propaniminoxy | OCH₃ | CH | 6-N(CH₃)₂ | H | H | H | |
| 1.169 | 2-Propaniminoxy | OCH₃ | CH | 5-N(CH₃)₂ | H | H | H | |
| 1.170 | 2-Propaniminoxy | OCH₃ | CH | 4-N(CH₃)₂ | H | H | H | |
| 1.171 | 2-Propaniminoxy | OCH₃ | CH | 3-N(CH₃)₂ | H | H | H | |
| 1.172 | OH | OCH₃ | CH | 6-N(C₂H₅)₂ | H | H | H | |

*measured in CDCl₃ or DMSO, δ in [ppm]

TABLE 2

| No. | R¹ | Y | R³ | X | R¹⁴ | R¹⁵ | R¹⁶ | R¹⁷ | Phys. data (m.p. [°C.] ¹H-NMR*, selected signals) |
|---|---|---|---|---|---|---|---|---|---|
| 2.001 | OH | O | OCH₃ | CH | 2-OCH₃ | H | H | H | 172–173 |
| 2.002 | OH | O | OCH₃ | CH | 4-OCH₃ | H | H | H | |
| 2.003 | OH | O | OCH₃ | CH | 5-OCH₃ | H | H | H | 168–169 |
| 2.004 | OH | O | OCH₃ | CH | 6-OCH₃ | H | H | H | 177 |
| 2.005 | 2-Propaniminoxy | O | OCH₃ | CH | 2-OCH₃ | H | H | H | |
| 2.006 | 2-Propaniminoxy | O | OCH₃ | CH | 4-OCH₃ | H | H | H | |
| 2.007 | 2-Propaniminoxy | O | OCH₃ | CH | 5-OCH₃ | H | H | H | 114–116 |
| 2.008 | 2-Propaniminoxy | O | OCH₃ | CH | 6-OCH₃ | H | H | H | δ=1.65(s), 4.85(s), 7.20(m), 1.95(s); 3.85(s); 3.98(s); 5.78(s); 6.77(d); 7.3–7.7(m); 8.25(d). |
| 2.009 | Benzyloxy | O | OCH₃ | CH | 2-OCH₃ | H | H | H | δ=3.70(s); 5.65(s), 6.95(m), 7.50(m), 8.13(m) |
| 2.010 | Benzyloxy | O | OCH₃ | CH | 4-OCH₃ | H | H | H | |
| 2.011 | Benzyloxy | O | OCH₃ | CH | 5-OCH₃ | H | H | H | |
| 2.012 | Benzyloxy | O | OCH₃ | CH | 6-OCH₃ | H | H | H | |
| 2.013 | OH | O | OCH₃ | CH | 2-OC₂H₅ | H | H | H | |
| 2.014 | OH | O | OCH₃ | CH | 4-OC₂H₅ | H | H | H | |
| 2.015 | OH | O | OCH₃ | CH | 5-OC₂H₅ | H | H | H | 156–158 |
| 2.016 | OH | O | OCH₃ | CH | 6-OC₂H₅ | H | H | H | |
| 2.017 | 2-Propaniminoxy | O | OCH₃ | CH | 2-OC₂H₅ | H | H | H | |
| 2.018 | 2-Propaniminoxy | O | OCH₃ | CH | 4-OC₂H₅ | H | H | H | |
| 2.019 | 2-Propaniminoxy | O | OCH₃ | CH | 5-OC₂H₅ | H | H | H | |
| 2.020 | 2-Propaniminoxy | O | OCH₃ | CH | 6-OC₂H₅ | H | H | H | |
| 2.021 | Benzyloxy | O | OCH₃ | CH | 2-OC₂H₅ | H | H | H | 92–93 |
| 2.022 | Benzyloxy | O | OCH₃ | CH | 4-OC₂H₅ | H | H | H | |
| 2.023 | Benzyloxy | O | OCH₃ | CH | 5-OC₂H₅ | H | H | H | |

TABLE 2-continued

| No. | R[1] | Y | R[3] | X | R[14] | R[15] | R[16] | R[17] | Phys. data (m.p. [°C.] $^1$H-NMR*, selected signals) |
|---|---|---|---|---|---|---|---|---|---|
| 2.024 | Benzyloxy | O | OCH$_3$ | CH | 6-OC$_2$H$_5$ | H | H | H | |
| 2.025 | OH | O | OCH$_3$ | CH | 2-O-n-C$_3$H$_7$ | H | H | H | |
| 2.026 | OH | O | OCH$_3$ | CH | 4-O-n-C$_3$H$_7$ | H | H | H | |
| 2.027 | OH | O | OCH$_3$ | CH | 5-O-n-C$_3$H$_7$ | H | H | H | |
| 2.028 | OH | O | OCH$_3$ | CH | 6-O-n-C$_3$H$_7$ | H | H | H | |
| 2.029 | 2-Propaniminoxy | O | OCH$_3$ | CH | 2-O-n-C$_3$H$_7$ | H | H | H | |
| 2.030 | 2-Propaniminoxy | O | OCH$_3$ | CH | 4-O-n-C$_3$H$_7$ | H | H | H | |
| 2.031 | 2-Propaniminoxy | O | OCH$_3$ | CH | 5-O-n-C$_3$H$_7$ | H | H | H | |
| 2.032 | 2-Propaniminoxy | O | OCH$_3$ | CH | 6-O-n-C$_3$H$_7$ | H | H | H | |
| 2.033 | Benzyloxy | O | OCH$_3$ | CH | 2-O-n-C$_3$H$_7$ | H | H | H | |
| 2.034 | Benzyloxy | O | OCH$_3$ | CH | 4-O-n-C$_3$H$_7$ | H | H | H | |
| 2.035 | Benzyloxy | O | OCH$_3$ | CH | 5-O-n-C$_3$H$_7$ | H | H | H | |
| 2.036 | Benzyloxy | O | OCH$_3$ | CH | 6-O-n-C$_3$H$_7$ | H | H | H | |
| 2.037 | OH | O | OCH$_3$ | CH | 2-O-i-C$_3$H$_7$ | H | H | H | |
| 2.038 | OH | O | OCH$_3$ | CH | 4-O-i-C$_3$H$_7$ | H | H | H | |
| 2.039 | OH | O | OCH$_3$ | CH | 5-O-i-C$_3$H$_7$ | H | H | H | 145–146 |
| 2.040 | OH | O | OCH$_3$ | CH | 6-O-i-C$_3$H$_7$ | H | H | H | 166 |
| 2.041 | 2-Propaniminoxy | O | OCH$_3$ | CH | 2-O-i-C$_3$H$_7$ | H | H | H | |
| 2.042 | 2-Propaniminoxy | O | OCH$_3$ | CH | 4-O-i-C$_3$H$_7$ | H | H | H | |
| 2.043 | 2-Propaniminoxy | O | OCH$_3$ | CH | 5-O-i-C$_3$H$_7$ | H | H | H | |
| 2.044 | 2-Propaniminoxy | O | OCH$_3$ | CH | 6-O-i-C$_3$H$_7$ | H | H | H | |
| 2.045 | Benzyloxy | O | OCH$_3$ | CH | 2-O-i-C$_3$H$_7$ | H | H | H | |
| 2.046 | Benzyloxy | O | OCH$_3$ | CH | 4-O-i-C$_3$H$_7$ | H | H | H | |
| 2.047 | Benzyloxy | O | OCH$_3$ | CH | 5-O-i-C$_3$H$_7$ | H | H | H | |
| 2.048 | Benzyloxy | O | OCH$_3$ | CH | 6-O-i-C$_3$H$_7$ | H | H | H | 65 |
| 2.049 | OH | O | OCH$_3$ | CH | 2-SCH$_3$ | H | H | H | 165 |
| 2.050 | OH | O | OCH$_3$ | CH | 4-SCH$_3$ | H | H | H | |
| 2.051 | OH | O | OCH$_3$ | CH | 5-SCH$_3$ | H | H | H | 157–158 |
| 2.052 | OH | O | OCH$_3$ | CH | 6-SCH$_3$ | H | H | H | |
| 2.053 | 2-Propaniminoxy | O | OCH$_3$ | CH | 2-SCH$_3$ | H | H | H | |
| 2.054 | 2-Propaniminoxy | O | OCH$_3$ | CH | 4-SCH$_3$ | H | H | H | |
| 2.055 | 2-Propaniminoxy | O | OCH$_3$ | CH | 5-SCH$_3$ | H | H | H | 125–126 |
| 2.056 | 2-Propaniminoxy | O | OCH$_3$ | CH | 6-SCH$_3$ | H | H | H | 127 |
| 2.057 | Benzyloxy | O | OCH$_3$ | CH | 2-SCH$_3$ | H | H | H | |
| 2.058 | Benzyloxy | O | OCH$_3$ | CH | 4-SCH$_3$ | H | H | H | |
| 2.059 | Benzyloxy | O | OCH$_3$ | CH | 5-SCH$_3$ | H | H | H | |
| 2.060 | Benzyloxy | O | OCH$_3$ | CH | 6-SCH$_3$ | H | H | H | 87 |
| 2.061 | OH | O | OCH$_3$ | CH | 2-SC$_2$H$_5$ | H | H | H | |
| 2.062 | OH | O | OCH$_3$ | CH | 4-SC$_2$H$_5$ | H | H | H | |
| 2.063 | OH | O | OCH$_3$ | CH | 5-SC$_2$H$_5$ | H | H | H | |
| 2.064 | OH | O | OCH$_3$ | CH | 6-SC$_2$H$_5$ | H | H | H | |
| 2.065 | 2-Propaniminoxy | O | OCH$_3$ | CH | 2-SC$_2$H$_5$ | H | H | H | |
| 2.066 | 2-Propaniminoxy | O | OCH$_3$ | CH | 4-SC$_2$H$_5$ | H | H | H | |
| 2.067 | 2-Propaniminoxy | O | OCH$_3$ | CH | 5-SC$_2$H$_5$ | H | H | H | |
| 2.068 | 2-Propaniminoxy | O | OCH$_3$ | CH | 6-SC$_2$H$_5$ | H | H | H | 94 |
| 2.069 | Benzyloxy | O | OCH$_3$ | CH | 2-SC$_2$H$_5$ | H | H | H | |
| 2.070 | Benzyloxy | O | OCH$_3$ | CH | 4-SC$_2$H$_5$ | H | H | H | |
| 2.071 | Benzyloxy | O | OCH$_3$ | CH | 5-SC$_2$H$_5$ | H | H | H | |
| 2.072 | Benzyloxy | O | OCH$_3$ | CH | 6-SC$_2$H$_5$ | H | H | H | δ=1.42(t), 3.20(q), 3.80(s), 4.99(s), 5.73(s), 7.0–7.6(m), 8.43(d) |
| 2.073 | OH | O | OCH$_3$ | CH | 2-S-n-C$_3$H$_7$ | H | H | H | |
| 2.074 | OH | O | OCH$_3$ | CH | 4-S-n-C$_3$H$_7$ | H | H | H | |
| 2.075 | OH | O | OCH$_3$ | CH | 5-S-n-C$_3$H$_7$ | H | H | H | |
| 2.076 | OH | O | OCH$_3$ | CH | 6-S-n-C$_3$H$_7$ | H | H | H | |
| 2.077 | 2-Propaniminoxy | O | OCH$_3$ | CH | 2-S-n-C$_3$H$_7$ | H | H | H | |
| 2.078 | 2-Propaniminoxy | O | OCH$_3$ | CH | 4-S-n-C$_3$H$_7$ | H | H | H | |
| 2.079 | 2-Propaniminoxy | O | OCH$_3$ | CH | 5-S-n-C$_3$H$_7$ | H | H | H | |
| 2.080 | 2-Propaniminoxy | O | OCH$_3$ | CH | 6-S-n-C$_3$H$_7$ | H | H | H | |
| 2.081 | Benzyloxy | O | OCH$_3$ | CH | 2-S-n-C$_3$H$_7$ | H | H | H | |

TABLE 2-continued

| No. | R¹ | Y | R³ | X | R¹⁴ | R¹⁵ | R¹⁶ | R¹⁷ | Phys. data (m.p. [°C.] ¹H-NMR*, selected signals) |
|---|---|---|---|---|---|---|---|---|---|
| 2.082 | Benzyloxy | O | OCH₃ | CH | 4-S-n-C₃H₇ | H | H | H | |
| 2.083 | Benzyloxy | O | OCH₃ | CH | 5-S-n-C₃H₇ | H | H | H | |
| 2.084 | Benzyloxy | O | OCH₃ | CH | 6-S-n-C₃H₇ | H | H | H | |
| 2.085 | OH | O | OCH₃ | CH | 2-S-i-C₃H₇ | H | H | H | |
| 2.086 | OH | O | OCH₃ | CH | 4-S-i-C₃H₇ | H | H | H | |
| 2.087 | OH | O | OCH₃ | CH | 5-S-i-C₃H₇ | H | H | H | |
| 2.088 | OH | O | OCH₃ | CH | 6-S-i-C₃H₇ | H | H | H | |
| 2.089 | 2-Propaniminoxy | O | OCH₃ | CH | 2-S-i-C₃H₇ | H | H | H | |
| 2.090 | 2-Propaniminoxy | O | OCH₃ | CH | 4-S-i-C₃H₇ | H | H | H | |
| 2.091 | 2-Propaniminoxy | O | OCH₃ | CH | 5-S-i-C₃H₇ | H | H | H | |
| 2.092 | 2-Propaniminoxy | O | OCH₃ | CH | 6-S-i-C₃H₇ | H | H | H | 99 |
| 2.093 | Benzyloxy | O | OCH₃ | CH | 2-S-i-C₃H₇ | H | H | H | |
| 2.094 | Benzyloxy | O | OCH₃ | CH | 4-S-i-C₃H₇ | H | H | H | |
| 2.095 | Benzyloxy | O | OCH₃ | CH | 5-S-i-C₃H₇ | H | H | H | |
| 2.096 | Benzyloxy | O | OCH₃ | CH | 6-S-i-C₃H₇ | H | H | H | |
| 2.097 | OH | O | OCH₃ | CH | 6-OCH₂CF₃ | H | H | H | 98 |
| 2.098 | 2-Propaniminoxy | O | OCH₃ | CH | 6-OCH₂CF₃ | H | H | H | 78 |
| 2.099 | Benzyloxy | O | OCH₃ | CH | 6-OCH₂CF₃ | H | H | H | |
| 2.100 | OH | O | OCH₃ | CH | 6-OCH₂CH₂OCH₃ | H | H | H | 116 |
| 2.101 | 2-Propaniminoxy | O | OCH₃ | CH | 6-OCH₂CH₂OCH₃ | H | H | H | 114 |
| 2.102 | Benzyloxy | O | OCH₃ | CH | 6-OCH₂CH₂OCH₃ | H | H | H | |
| 2.103 | OH | O | OCH₃ | CH | 6-OCH₂CH₂N(CH₃)₂ | H | H | H | |
| 2.104 | 2-Propaniminoxy | O | OCH₃ | CH | 6-OCH₂CH₂N(CH₃)₂ | H | H | H | |
| 2.105 | Benzyloxy | O | OCH₃ | CH | 6-OCH₂CH₂N(CH₃)₂ | H | H | H | |
| 2.106 | OH | O | OCH₃ | CH | 6-ON(CH₃)₂ | H | H | H | |
| 2.107 | 2-Propaniminoxy | O | OCH₃ | CH | 6-ON(CH₃)₂ | H | H | H | |
| 2.108 | Benzyloxy | O | OCH₃ | CH | 6-ON(CH₃)₂ | H | H | H | |
| 2.109 | OCH₂CF₃ | O | OCH₃ | CH | 2-OCH₃ | H | H | H | |
| 2.110 | OCH₂CF₃ | O | OCH₃ | CH | 4-OCH₃ | H | H | H | |
| 2.111 | OCH₂CF₃ | O | OCH₃ | CH | 5-OCH₃ | H | H | H | |
| 2.112 | OCH₂CF₃ | O | OCH₃ | CH | 6-OCH₃ | H | H | H | |
| 2.113 | Propargyloxy | O | OCH₃ | CH | 2-OCH₃ | H | H | H | |
| 2.114 | Propargyloxy | O | OCH₃ | CH | 4-OCH₃ | H | H | H | |
| 2.115 | Propargyloxy | O | OCH₃ | CH | 5-OCH₃ | H | H | H | |
| 2.116 | Propargyloxy | O | OCH₃ | CH | 6-OCH₃ | H | H | H | |
| 2.117 | Allyloxy | O | OCH₃ | CH | 2-OCH₃ | H | H | H | |
| 2.118 | Allyloxy | O | OCH₃ | CH | 4-OCH₃ | H | H | H | |
| 2.119 | Allyloxy | O | OCH₃ | CH | 5-OCH₃ | H | H | H | |
| 2.120 | Allyloxy | O | OCH₃ | CH | 6-OCH₃ | H | H | H | |
| 2.121 | OH | O | OCH₂CH₂ | | 2-OCH₃ | H | H | H | |
| 2.122 | OH | O | OCH₂CH₂ | | 4-OCH₃ | H | H | H | |
| 2.123 | OH | O | OCH₂CH₂ | | 5-OCH₃ | H | H | H | |
| 2.124 | OH | O | OCH₂CH₂ | | 6-OCH₃ | H | H | H | |
| 2.125 | OH | O | OCH₃ | CF | 2-OCH₃ | H | H | H | |
| 2.126 | OH | O | OCH₃ | CF | 4-OCH₃ | H | H | H | |
| 2.127 | OH | O | OCH₃ | CF | 5-OCH₃ | H | H | H | |
| 2.128 | OH | O | OCH₃ | CF | 6-OCH₃ | H | H | H | |
| 2.129 | OH | O | OCH₃ | CH | 2-SCH₃ | 4-CH₃ | H | H | |
| 2.130 | OH | O | OCH₃ | CH | 2-SCH₃ | 5-CH₃ | H | H | |
| 2.131 | OH | O | OCH₃ | CH | 2-SCH₃ | 6-CH₃ | H | H | |
| 2.132 | OH | O | OCH₃ | CH | 4-SCH₃ | 2-CH₃ | H | H | |
| 2.133 | OH | O | OCH₃ | CH | 4-SCH₃ | 5-CH₃ | H | H | |
| 2.134 | OH | O | OCH₃ | CH | 4-SCH₃ | 6-CH₃ | H | H | |
| 2.135 | OH | O | OCH₃ | CH | 5-SCH₃ | 4-CH₃ | H | H | |
| 2.136 | OH | O | OCH₃ | CH | 5-SCH₃ | 2-CH₃ | H | H | |
| 2.137 | OH | O | OCH₃ | CH | 5-SCH₃ | 6-CH₃ | H | H | |
| 2.138 | OH | O | OCH₃ | CH | 6-SCH₃ | 4-CH₃ | H | H | |
| 2.139 | OH | O | OCH₃ | CH | 6-SCH₃ | 5-CH₃ | H | H | |
| 2.140 | OH | O | OCH₃ | CH | 6-SCH₃ | 2-CH₃ | H | H | |
| 2.141 | OH | O | OCH₃ | CH | 2-OCH₃ | 4-CH₃ | H | H | |
| 2.112 | OH | O | OCH₃ | CH | 2-OCH₃ | 5-CH₃ | H | H | |
| 2.143 | OH | O | OCH₃ | CH | 2-OCH₃ | 6-CH₃ | H | H | |

TABLE 2-continued

| No. | R¹ | Y | R³ | X | R¹⁴ | R¹⁵ | R¹⁶ | R¹⁷ | Phys. data (m.p. [°C.] ¹H-NMR*, selected signals) |
|---|---|---|---|---|---|---|---|---|---|
| 2.144 | OH | O | OCH₃ | CH | 4-OCH₃ | 2-CH₃ | H | H | |
| 2.145 | OH | O | OCH₃ | CH | 4-OCH₃ | 5-CH₃ | H | H | |
| 2.146 | OH | O | OCH₃ | CH | 4-OCH₃ | 6-CH₃ | H | H | |
| 2.147 | OH | O | OCH₃ | CH | 5-OCH₃ | 4-CH₃ | H | H | |
| 2.148 | OH | O | OCH₃ | CH | 5-OCH₃ | 2-CH₃ | H | H | |
| 2.149 | OH | O | OCH₃ | CH | 5-OCH₃ | 6-CH₃ | H | H | |
| 2.150 | OH | O | OCH₃ | CH | 6-OCH₃ | 4-CH₃ | H | H | |
| 2.151 | OH | O | OCH₃ | CH | 2-OCH₃ | 6-OCH₃ | H | H | |
| 2.152 | OH | O | OCH₃ | CH | 2-OCH₃ | 6-F | H | H | |
| 2.153 | OH | O | OCH₃ | CH | 2-OCH₃ | 6-Cl | H | H | |
| 2.154 | OH | O | OCH₃ | CH | 6-OCH₃ | 2-Cl | H | H | |
| 2.155 | OH | O | OCH₃ | CH | 2-OCH₃ | 5-OCH₃ | H | H | |
| 2.156 | OH | O | OCH₃ | CH | 4-OCH₃ | 6-SCH₃ | H | H | |
| 2.157 | OH | O | OCH₃ | CH | 6-OCH₃ | 5-CH₃ | H | H | 179–181 |
| 2.158 | OH | O | OCH₃ | CH | 6-OCH₃ | 2-CH₃ | H | H | |
| 2.159 | Methoxy | O | OCH₃ | CH | 2-OCH₃ | H | H | H | 159–160 |
| 2.160 | 2,2,2-Trifluoro-ethoxy | O | OCH₃ | CH | 6-S-i-C₃H₇ | H | H | H | 83 |
| 2.161 | 2-Propaniminoxy | O | OCH₃ | N | 6-OCH₂CH₂OCH₃ | H | H | H | 125 |
| 2.162 | Benzyloxy | O | OCH₃ | CH | 6-OCH₂CF₃ | H | H | H | 78 |
| 2.163 | OH | O | OCH₃ | CH | 6-N(CH₃)₂ | H | H | H | |
| 2.164 | 2-Propaniminoxy | O | OCH₃ | CH | 6-N(CH₃)₂ | H | H | H | |
| 2.165 | Benzyloxy | O | OCH₃ | CH | 6-N(CH₃)₂ | H | H | H | |

*measured in CDCl₃ or DMSO, δ in [ppm]

TABLE 3

| No. | R¹ | Y | R³ | X | R¹⁴ | R¹⁵ | R¹⁶ | R¹⁷ |
|---|---|---|---|---|---|---|---|---|
| 3.001 | OH | O | OCH₃ | CH | 3-OCH₃ | H | H | H |
| 3.002 | OH | O | OCH₃ | CH | 2-OCH₃ | H | H | H |
| 3.003 | 1-Imidazolyl | O | OCH₃ | CH | 3-OCH₃ | H | H | H |
| 3.004 | 1-Imidazolyl | O | OCH₃ | CH | 2-OCH₃ | H | H | H |
| 3.005 | 2-Propaniminoxy | O | OCH₃ | CH | 3-OCH₃ | H | H | H |
| 3.006 | 2-Propaniminoxy | O | OCH₃ | CH | 2-OCH₃ | H | H | H |
| 3.007 | Methylthiomethyl | O | OCH₃ | CH | 3-OCH₃ | H | H | H |
| 3.008 | Methylthiomethyl | O | OCH₃ | CH | 2-OCH₃ | H | H | H |
| 3.009 | Benzyloxy | O | OCH₃ | CH | 3-OCH₃ | H | H | H |
| 3.010 | Benzyloxy | O | OCH₃ | CH | 2-OCH₃ | H | H | H |
| 3.011 | Cyclohexaniminoxy | O | OCH₃ | CH | 3-OCH₃ | H | H | H |
| 3.012 | Cyclohexaniminoxy | O | OCH₃ | CH | 2-OCH₃ | H | H | H |
| 3.013 | OH | O | OCH₃ | CH | 3-OC₂H₅ | H | H | H |
| 3.014 | OH | O | OCH₃ | CH | 2-OC₂H₅ | H | H | H |
| 3.015 | 2-Propaniminoxy | O | OCH₃ | CH | 3-OC₂H₅ | H | H | H |
| 3.016 | 2-Propaniminoxy | O | OCH₃ | CH | 2-OC₂H₅ | H | H | H |
| 3.017 | Benzyloxy | O | OCH₃ | CH | 3-OC₂H₅ | H | H | H |
| 3.018 | Benzyloxy | O | OCH₃ | CH | 2-OC₂H₅ | H | H | H |
| 3.019 | OH | O | OCH₃ | CH | 3-O-n-C₃H₇ | H | H | H |

TABLE 3-continued

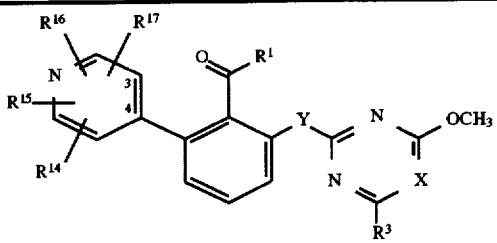

| No. | R$^1$ | Y | R$^3$ | X | R$^{14}$ | R$^{15}$ | R$^{16}$ | R$^{17}$ |
|---|---|---|---|---|---|---|---|---|
| 3.020 | OH | O | OCH$_3$ | CH | 2-O-n-C$_3$H$_7$ | H | H | H |
| 3.021 | 2-Propaniminoxy | O | OCH$_3$ | CH | 3-O-n-C$_3$H$_7$ | H | H | H |
| 3.022 | 2-Propaniminoxy | O | OCH$_3$ | CH | 2-O-n-C$_3$H$_7$ | H | H | H |
| 3.023 | Benzyloxy | O | OCH$_3$ | CH | 3-O-n-C$_3$H$_7$ | H | H | H |
| 3.024 | Benzyloxy | O | OCH$_3$ | CH | 2-O-n-C$_3$H$_7$ | H | H | H |
| 3.025 | OH | O | OCH$_3$ | CH | 3-O-i-C$_3$H$_7$ | H | H | H |
| 3.026 | OH | O | OCH$_3$ | CH | 2-O-i-C$_3$H$_7$ | H | H | H |
| 3.027 | 2-Propaniminoxy | O | OCH$_3$ | CH | 3-O-i-C$_3$H$_7$ | H | H | H |
| 3.028 | 2-Propaniminoxy | O | OCH$_3$ | CH | 2-O-i-C$_3$H$_7$ | H | H | H |
| 3.029 | Benzyloxy | O | OCH$_3$ | CH | 3-O-i-C$_3$H$_7$ | H | H | H |
| 3.030 | Benzyloxy | O | OCH$_3$ | CH | 2-O-i-C$_3$H$_7$ | H | H | H |
| 3.031 | OH | O | OCH$_3$ | CH | 3-SCH$_3$ | H | H | H |
| 3.032 | OH | O | OCH$_3$ | CH | 2-SCH$_3$ | H | H | H |
| 3.033 | 2-Propaniminoxy | O | OCH$_3$ | CH | 3-SCH$_3$ | H | H | H |
| 3.034 | 2-Propaniminoxy | O | OCH$_3$ | CH | 2-SCH$_3$ | H | H | H |
| 3.035 | Benzyloxy | O | OCH$_3$ | CH | 3-SCH$_3$ | H | H | H |
| 3.036 | Benzyloxy | O | OCH$_3$ | CH | 2-SCH$_3$ | H | H | H |
| 3.037 | OH | O | OCH$_3$ | CH | 3-SC$_2$H$_5$ | H | H | H |
| 3.038 | OH | O | OCH$_3$ | CH | 2-SC$_2$H$_5$ | H | H | H |
| 3.039 | 2-Propaniminoxy | O | OCH$_3$ | CH | 3-SC$_2$H$_5$ | H | H | H |
| 3.040 | 2-Propaniminoxy | O | OCH$_3$ | CH | 2-SC$_2$H$_5$ | H | H | H |
| 3.041 | Benzyloxy | O | OCH$_3$ | CH | 3-SC$_2$H$_5$ | H | H | H |
| 3.042 | Benzyloxy | O | OCH$_3$ | CH | 2-SC$_2$H$_5$ | H | H | H |
| 3.043 | OH | O | OCH$_3$ | CH | 3-S-n-C$_3$H$_7$ | H | H | H |
| 3.044 | OH | O | OCH$_3$ | CH | 2-S-n-C$_3$H$_7$ | H | H | H |
| 3.045 | 2-Propaniminoxy | O | OCH$_3$ | CH | 3-S-n-C$_3$H$_7$ | H | H | H |
| 3.046 | 2-Propaniminoxy | O | OCH$_3$ | CH | 2-S-n-C$_3$H$_7$ | H | H | H |
| 3.047 | Benzyloxy | O | OCH$_3$ | CH | 3-S-n-C$_3$H$_7$ | H | H | H |
| 3.048 | Benzyloxy | O | OCH$_3$ | CH | 2-S-n-C$_3$H$_7$ | H | H | H |
| 3.049 | OH | O | OCH$_3$ | CH | 3-S-i-C$_3$H$_7$ | H | H | H |
| 3.050 | OH | O | OCH$_3$ | CH | 2-S-i-C$_3$H$_7$ | H | H | H |
| 3.051 | 2-Propaniminoxy | O | OCH$_3$ | CH | 3-S-i-C$_3$H$_7$ | H | H | H |
| 3.052 | 2-Propaniminoxy | O | OCH$_3$ | CH | 2-S-i-C$_3$H$_7$ | H | H | H |
| 3.053 | Benzyloxy | O | OCH$_3$ | CH | 3-S-i-C$_3$H$_7$ | H | H | H |
| 3.054 | Benzyloxy | O | OCH$_3$ | CH | 2-S-i-C$_3$H$_7$ | H | H | H |
| 3.055 | OH | O | OCH$_3$ | CH | 6-OCH$_2$CF$_3$ | H | H | H |
| 3.056 | 2-Propaniminoxy | O | OCH$_3$ | CH | 6-OCH$_2$CF$_3$ | H | H | H |
| 3.057 | Benzyloxy | O | OCH$_3$ | CH | 6-OCH$_2$CF$_3$ | H | H | H |
| 3.058 | OH | O | OCH$_3$ | CH | 6-OCH$_2$CH$_2$OCH$_3$ | H | H | H |
| 3.059 | 2-Propaniminoxy | O | OCH$_3$ | CH | 6-OCH$_2$CH$_2$OCH$_3$ | H | H | H |
| 3.060 | Benzyloxy | O | OCH$_3$ | CH | 6-OCH$_2$CH$_2$OCH$_3$ | H | H | H |
| 3.061 | OH | O | OCH$_3$ | CH | 6-OCH$_2$CH$_2$N(CH$_3$)$_2$ | H | H | H |
| 3.062 | 2-Propaniminoxy | O | OCH$_3$ | CH | 6-OCH$_2$CH$_2$N(CH$_3$)$_2$ | H | H | H |
| 3.063 | Benzyloxy | O | OCH$_3$ | CH | 6-OCH$_2$CH$_2$N(CH$_3$)$_2$ | H | H | H |
| 3.064 | OH | O | OCH$_3$ | CH | 6-ON(CH$_3$)$_2$ | H | H | H |
| 3.065 | 2-Propaniminoxy | O | OCH$_3$ | CH | 6-ON(CH$_3$)$_2$ | H | H | H |
| 3.066 | Benzyloxy | O | OCH$_3$ | CH | 6-ON(CH$_3$)$_2$ | H | H | H |
| 3.067 | OCH$_2$CF$_3$ | O | OCH$_3$ | CH | 3-OCH$_3$ | H | H | H |
| 3.068 | OCH$_2$CF$_3$ | O | OCH$_3$ | CH | 2-OCH$_3$ | H | H | H |
| 3.069 | Propargyloxy | O | OCH$_3$ | CH | 3-OCH$_3$ | H | H | H |
| 3.070 | Propargyloxy | O | OCH$_3$ | CH | 2-OCH$_3$ | H | H | H |
| 3.071 | Allyloxy | O | OCH$_3$ | CH | 3-OCH$_3$ | H | H | H |
| 3.072 | Allyloxy | O | OCH$_3$ | CH | 2-OCH$_3$ | H | H | H |
| 3.073 | OH | O | OCH$_2$CH$_2$ | | 3-OCH$_3$ | H | H | H |
| 3.074 | OH | O | OCH$_2$CH$_2$ | | 2-OCH$_3$ | H | H | H |
| 3.075 | OH | O | OCH$_3$ | CF | 3-OCH$_3$ | H | H | H |
| 3.076 | OH | O | OCH$_3$ | CF | 2-OCH$_3$ | H | H | H |
| 3.077 | OH | O | OCH$_3$ | CH | 3-OCH$_3$ | 2-CH$_3$ | H | H |
| 3.078 | OH | O | OCH$_3$ | CH | 3-OCH$_3$ | 5-CH$_3$ | H | H |
| 3.079 | OH | O | OCH$_3$ | CH | 3-OCH$_3$ | 6-CH$_3$ | H | H |
| 3.080 | OH | O | OCH$_3$ | CH | 2-OCH$_3$ | 3-CH$_3$ | H | H |
| 3.081 | OH | O | OCH$_3$ | CH | 2-OCH$_3$ | 5-CH$_3$ | H | H |
| 3.082 | OH | O | OCH$_3$ | CH | 2-OCH$_3$ | 6-CH$_3$ | H | H |
| 3.083 | 2-Propaniminoxy | O | OCH$_3$ | CH | 3-OCH$_3$ | 2-CH$_3$ | H | H |
| 3.084 | 2-Propaniminoxy | O | OCH$_3$ | CH | 3-OCH$_3$ | 5-CH$_3$ | H | H |

TABLE 3-continued

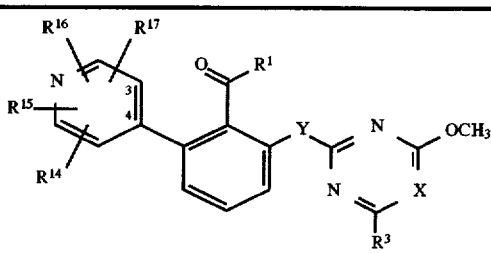

| No. | R¹ | Y | R³ | X | R¹⁴ | R¹⁵ | R¹⁶ | R¹⁷ |
|---|---|---|---|---|---|---|---|---|
| 3.085 | 2-Propaniminoxy | O | $OCH_3$ | CH | 3-$OCH_3$ | 6-$CH_3$ | H | H |
| 3.086 | 2-Propaniminoxy | O | $OCH_3$ | CH | 2-$OCH_3$ | 3-$CH_3$ | H | H |
| 3.087 | 2-Propaniminoxy | O | $OCH_3$ | CH | 2-$OCH_3$ | 5-$CH_3$ | H | H |
| 3.088 | 2-Propaniminoxy | O | $OCH_3$ | CH | 2-$OCH_3$ | 6-$CH_3$ | H | H |
| 3.089 | OH | O | $OCH_3$ | CH | 2-$OCH_3$ | 6-$OCH_3$ | H | H |
| 3.090 | OH | O | $OCH_3$ | CH | 2-$OCH_3$ | 6-F | H | H |
| 3.091 | OH | O | $OCH_3$ | CH | 2-$OCH_3$ | 3-$OCH_3$ | H | H |
| 3.092 | OH | O | $OCH_3$ | CH | 2-$OCH_3$ | 5-$OCH_3$ | H | H |
| 3.093 | OH | O | $OCH_3$ | CH | 2-$OC_2H_5$ | 6-$OC_2H_5$ | H | H |
| 3.094 | OH | O | $OCH_3$ | CH | 2-$OCH_3$ | 6-Cl | H | H |
| 3.095 | OH | O | $OCH_3$ | CH | 2-$SCH_3$ | 6-$OCH_3$ | H | H |
| 3.096 | OH | O | $OCH_3$ | CH | 2-$SCH_3$ | 6-$SCH_3$ | H | H |
| 3.097 | OH | O | $OCH_3$ | CH | 2-Cl | 6-$OC_2H_5$ | H | H |
| 3.098 | OH | O | $OCH_3$ | CH | 2-Cl | 3-$OCH_3$ | H | H |

TABLE 4

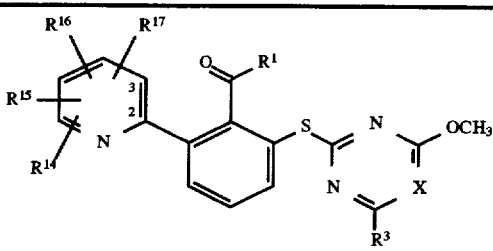

Compounds of the abovementioned formula, in which the combination of the substituents $R^1$, $R^3$, X and $R^{14}$–$R^{17}$ for one compound in each case corresponds to one line of Table 1. Table 4 therefore relates to compounds having the numbers 4.001 to 4.158. No. 4.001 corresponding to No. 1.001 from Table 1, but with Y=S instead of O. Compound No. 4.008 ($R^1$ =2-propaniminoxy, $R^3$ =$OCH_3$, X=CH, 14 =6—$OCH_3$, $R^{15}$–$R^{17}$ =H) has a melting point of 130°–132 °C.

TABLE 5

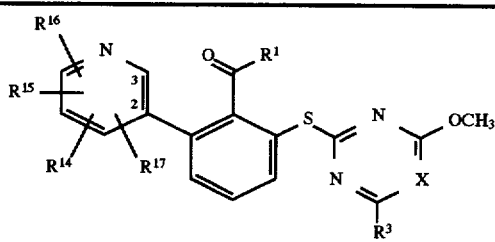

Compounds of the abovementioned formula, in which the combination of the substituents $R^1$, $R^3$, X and $R^{14}$–$R^{17}$ for one compound in each case corresponds to one line of Table 2. Table 5 therefore relates to compounds having the numbers 5.001 to 5.158. No. 5.001 corresponding to No. 2.001 from Table 2, but with Y=S instead of O.

TABLE 6

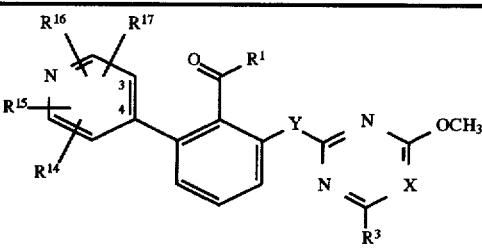

Compounds of the abovementioned formula, in which the combination of the substituents $R^1$, $R^3$, X and $R^{14}$–$R^{17}$ for one compound in each case corresponds to one line of Table 3. Table 6 therefore relates to compounds having the numbers 6.001 to 6.098. No. 6.001 corresponding to No. 3.001 from Table 3, but with Y=S instead of O.

Use Examples p It was possible to show the herbicidal and growth-regulatory action of the compounds of the formula I by greenhouse tests:

The cultivation containers used were plastic pots containing loamy sand with about 3.0% humus as a substrate. The seeds of the test plants were sown separately according to species.

In the case of pre-emergence treatment, the active compounds suspended or emulsified in water were applied directly after sowing by means of finely dispersing nozzles. The containers were lightly watered in order to promote germination and growth and then covered with transparent plastic hoods until the plants had taken root. This covering causes a uniform germination of the test plants if this has not been adversely affected by the active compounds.

For the purpose of post-emergence treatment, the test plants, depending on growth form, were first raised to a growth height of from 3 to 15 cm and only then treated with the active compounds suspended or emulsified in water. To do this, the test plants were either sown directly and raised in the same containers or they were first raised separately as seed plants and transplanted into the test containers a few days before the treatment. The application rate for post-emergence treatment was 0.0313 or 0.0625 kg/ha of a.s. respectively.

The plants were kept in a species-specific manner at 10°–25° C. or 20°–35° C. The test period extended over 2 to 4 weeks. During this time the plants were tended, and their reaction to the individual treatments was assessed.

The herbicidal action was assessed on a scale of from 0 to 100. 100 here means no emergence of the plants or complete destruction at least of the above-ground parts and 0 means no damage or normal course of growth.

The growth-regulating action was determined by height measurement. At the end of the test, the growth heights of the treated plants were measured and related to the growth heights of untreated plants.

The plants used in the greenhouse tests are composed of the following species:

| Botanical name | Common name |
| --- | --- |
| Alopecurus myosuroides | blackgrass |
| Echinochloa crus-galli | barnyardgrass |
| Setaria italica | foxtail millet |
| Sinapis alba | white mustard |
| Solanum nigrum | black nightshade |
| Veronica spp. | speedwell |

The results show a very good herbicidal action of the compound No. 1.004 according to the invention.

The better herbicidal action compared with compounds of the prior art emerges from Tables I and II below. The comparison substances A and B used were compounds of the following structure:

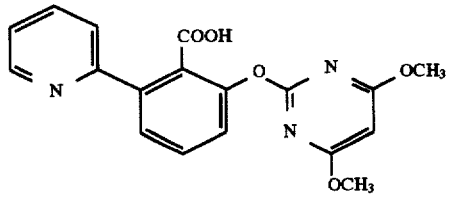

A

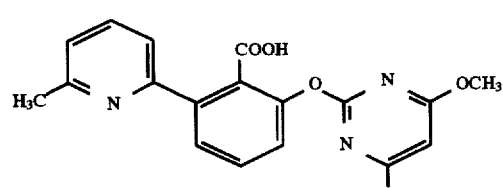

B

TABLE I

Herbicidal activity on post-emergence application at 0.0625 or 0.0313 kg/ha of a.s. respectively in the greenhouse

| | Damage in % | | | |
| --- | --- | --- | --- | --- |
| Test | 1.004 | | A | |
| plants | 0.0625 kg/ha | 0.0313 kg/ha | 0.0625 kg/ha | 0.0313 kg/ha |
| Setaria | 80 | 80 | 50 | 50 |

TABLE I-continued

Herbicidal activity on post-emergence application at 0.0625 or 0.0313 kg/ha of a.s. respectively in the greenhouse

| | Damage in % | | | |
| --- | --- | --- | --- | --- |
| Test | 1.004 | | A | |
| plants | 0.0625 kg/ha | 0.0313 kg/ha | 0.0625 kg/ha | 0.0313 kg/ha |
| viridis | | | | |
| Sinapis alba | 100 | 100 | 90 | 85 |
| Solanum nigrum | 100 | 100 | 98 | 80 |
| Veronica spp. | 100 | 100 | 80 | 80 |

TABLE II

Herbicidal activity on post-emergence application at 0.0156 or 0.0078 kg/ha of a.s. respectively in the greenhouse

| | Damage in % | | | |
| --- | --- | --- | --- | --- |
| Test | 1.004 | | B | |
| plants | 0.0156 kg/ha | 0.0078 kg/ha | 0.0156 kg/ha | 0.0078 kg/ha |
| Echinochloa crus-galli | 95 | 90 | 80 | 60 |
| Sinapis alba | 98 | 98 | 95 | 90 |
| Stellaria media | 100 | 80 | 50 | 30 |
| Veronica spp. | 100 | 100 | 20 | 15 |

We claim:

1. A substituted pyridylsalicylaldehyde or —salicylic acid derivative of the formula I

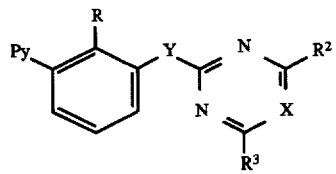

(I)

where the substituents have the following meanings:

R is

and where $R^1$ has the following meanings:
 a) hydrogen;
 b) a succinylimidoxy group;
 c) a 5-membered heteroaromatic linked via a nitrogen atom and containing two to three nitrogen atoms, which can carry one to two halogen atoms and/or one to two of the following radicals:
  $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;
 d) a radical —(O)$_m$NR$^6$R$^7$, where m is 0 or 1 and $R^6$ and $R^7$, which can be identical or different, have the following meanings:
  hydrogen;
  $C_1$–$C_8$-alkyl, $C_3$–$C_6$-alkenyl, $C_3$–$C_6$-alkynyl, $C_3$–$C_8$-cycloalkyl, these radicals in each case being able to carry one to five halogen atoms and/or one to two of the following groups: $C_1-C_4$-alkyl, $C_1-C_4$-alkoxy, $C_3-C_6$-alkenyloxy, $C_3-C_6$-alkynyloxy, $C_1-C_4$-alkylthio, $C_3-C_6$-alkenylthio, $C_3-C_6$-alkynylthio, $C_1-C_4$-haloalkoxy, $C_1-C_4$-alkylcarbonyl, $C_3-C_6$-alkenylcarbonyl, $C_3-C_6$-alkynylcarbonyl, $C_1-C_4$-alkoxycarbonyl, $C_3-C_6$-alkenyloxycarbonyl, $C_3-C_6$-alkynyloxy- carbonyl, di-($C_1-C_4$-alkyl) amino, $C_3-C_8$-cycloalkyl, phenyl or phenyl which is mono- or polysubstituted by halogen, nitro, cyano, $C_1-C_4$-alkyl, $C_1-C_4$-haloalkyl, $C_1-C_4$-alkoxy, $C_1-C_4$-haloalkoxy or $C_1-C_4$-alkylthio;

phenyl which can be substituted by one or more of the following radicals: halogen, nitro, cyano, $C_1-C_4$-alkyl, $C_1-C_4$-haloalkyl, $C_1-C_4$-alkoxy, $C_1-C_4$-haloalkoxy or $C_1-C_4$-alkylthio;

$R^6$ and $R^7$ together are an unsubstituted or substituted $C_4-C_7$-alkylene chain closed to give a ring or together are an unsubstituted or substituted $C_3-C_6$-alkylene chain which is closed to give a ring and contains a heteroatom selected from the group consisting of oxygen, sulfur and nitrogen;

e) $R^1$ is additionally a group

where $R^8$ is $C_1-C_4$-alkyl, phenyl, phenyl which is mono- or polysubstituted by halogen, nitro, cyano, $C_1-C_4$-alkyl, $C_1-C_4$-haloalkyl, $C_1-C_4$-alkoxy, $C_1-C_4$-haloalkoxy or $C_1-C_4$-alkylthio, or $C_1-C_4$-haloalkyl, $C_3-C_6$-alkenyl or $C_3-C_6$-alkynyl, p assumes the values 1, 2, 3 or 4 and k assumes the values 0, 1 or 2;

f) a radical $OR^9$, where $R^9$ is:
i) hydrogen, an alkali metal cation, the equivalent of an alkaline earth metal cation, the ammonium cation or an organic ammonium ion;
ii) a $C_3-C_8$-cycloalkyl group, which can carry one to three $C_1-C_4$-alkyl radicals;
iii) a $C_1-C_8$-alkyl group, which can carry one to five halogen atoms and/or one of the following radicals:
$C_1-C_4$-alkoxy, $C_1-C_4$-alkylthio, cyano, $C_1-C_4$-alkylcarbonyl, $C_3-C_8$-cycloalkyl, $C_1-C_4$-alkoxycarbonyl, phenyl, or phenyl or phenoxy which is mono- or polysubstituted by halogen, nitro, cyano, $C_1-C_4$-alkyl, $C_1-C_4$-haloalkyl, $C_1-C_4$-alkoxy, $C_1-C_4$-haloalkoxy and/ or $C_1-C_4$-alkylthio;
iv) a $C_1-C_8$-alkyl group, which can carry one to five halogen atoms and carries one of the following radicals: a 5-membered heteroaromatic, containing one to three nitrogen atoms, or a 5-membered heteroaromatic, containing one nitro atom and an oxygen or sulfur atom, which can carry one to four halogen atoms and/or one to two of the following radicals: nitro, cyano, $C_1-C_4$-alkyl, $C_1-C_4$-haloalkyl, $C_1-C_4$-alkoxy, $C_1-C_4$-haloalkoxy and/or $C_1-C_4$-alkylthio;
v) a $C_2-C_6$-alkyl group, which in the 2-position carries one of the following radicals: $C_1-C_4$-alkoxyimino, $C_3-C_6$-alkenyloxyimino, $C_3-C_6$-haloalkenyloxyimino or benzyloxyimino;
vi) a $C_3-C_6$-alkenyl group or a $C_3-C_6$-alkynyl group, where these groups in turn can carry one to five halogen atoms;
vii) a phenyl radical which can carry one to five halogen atoms and/or one to three of the following radicals: nitro, cyano, $C_1-C_4$-alkyl, $C_1-C_4$-haloalkyl, $C_1-C_4$-alkoxy, $C_1-C_4$-haloalkoxy and/or $C_1-C_4$-alkylthio;
viii) a 5-membered heteroaromatic linked via a nitrogen atom and containing one to three nitrogen atoms, which can carry one to two halogen atoms and/or one to two of the following radicals: nitro, cyano, $C_1-C_4$-alkyl, $C_1-C_4$-haloalkyl, $C_1-C_4$-alkoxy, $C_1-C_4$-haloalkoxy and/or $C_1-C_4$-alkylthio;
ix) $R^9$ is additionally a group $-N=CR^{10}R^{11}$, where $R_{10}$ and $R^{11}$, which can be identical or different, are:
$C_1-C_{12}$-alkyl, $C_3-C_6$-alkenyl, $C_3-C_6$-alkynyl, $C_3-C_8$-cycloalkyl, these radicals being able to carry a $C_1-C_4$-alkoxy or $C_1-C_4$-alkylthio radical and/or a phenyl radical;
phenyl which can be substituted by one or more of the following radicals: halogen, nitro, cyano, $C_1-C_4$-alkyl, $C_1-C_4$-haloalkyl, $C_1-C_4$-alkoxy, $C_1-C_4$-haloalkoxy or $C_1-C_4$-alkylthio;
or $R^{10}$ and $R^{11}$ together form a $C_3-C_{12}$-alkylene chain which can carry one to three $C_1-C_4$-alkyl groups;

g) or $R^1$ forms a radical $-NH-SO_2-R^{12}$, where $R^{12}$ is:
$C_1-C_4$-alkyl, $C_1-C_4$-haloalkyl, $C_3-C_6$-alkenyl, $C_3-C_6$-alkynyl, $C_3-C_8$-cycloalkyl, these radicals being able to carry a $C_1-C_4$-alkoxy or $C_1-C_4$-alkylthio radical and/or a phenyl radical;
phenyl which can be substituted by one or more of the following radicals: halogen, nitro, cyano, $C_1-C_4$-alkyl, $C_1-C_4$-haloalkyl, $C_1-C_4$-alkoxy, $C_1-C_4$-haloalkoxy or $C_1-C_4$-alkylthio;

$R^2$ is halogen, $C_1-C_4$-alkyl, $C_1-C_4$-haloalkyl, $C_1-C_4$-alkoxy, $C_1-C_4$-haloalkoxy or $C_1-C_4$-alkylthio;

X is $CR^{13}$, $R^{13}$ being hydrogen or halogen or together with $R^3$ forming a 3- to 4-membered alkylene or alkenylene chain in which one methylene group in each case is replaced by oxygen;

$R^3$ is halogen, $C_1-C_4$-alkyl, $C_1-C_4$-haloalkyl, $C_1-C_4$-alkoxy, $C_1-C_4$-haloalkoxy or $C_1-C_4$-alkylthio, or $R^3$ is linked with $R^{13}$ as indicated above to give a 5- or 6-membered ring;

Y is oxygen or sulfur;

Py is a pyridine ring linked in any desired C-position, which carries four substituents $R^{14}$, $R^{15}$, $R^{16}$ and $R^{17}$, $R^{14}$ is a $C_1-C_8$-alkoxy group, which can carry one to five halogen atoms and/or one of the following radicals: $C_1-C_4$-alkoxy, $C_1-C_4$-halogenalkoxy, $C_1-C_4$-alkylthio, cyano, $C_3-C_8$-cycloalkyl or di-$C_1-C_4$-alkylamino;

$R^{15}$, $R^{16}$ and $R^{17}$ are in each case independently of one another, hydrogen, nitro, halogen, $C_1-C_8$-alkyl, $C_1-C_8$-haloalkyl and the radicals mentioned for $R^{14}$.

2. A substituted pyridylsalicylaldehyde or —salicylic acid derivative of the formula I as defined in claim 1, where at least two of the radicals $R^{15}$ to $R^{17}$ are hydrogen.

3. A substituted pyridylsalicylaldehyde or —salicylic acid derivative of the formula I as defined in claim 1, where $R^3$ is methoxy and X is CH or CF, or $R^3$ is linked with X to give an —$OCH_2CH_2$—chain.

4. A substituted pyridylsalicylaldehyde or —salicylic acid derivative of the formula I as defined in claim 1, where two of the radicals $R^{15}$ to $R^{17}$ are hydrogen and the remaining radical is a $C_1$–$C_4$-alkyl group.

5. A herbicidal composition or composition for influencing plant growth, which contains at least one pyridylsalicylaldehyde or —salicylic acid derivative of the formula I as defined in claim 1 and customary inert carriers.

6. A process for controlling undesired plant growth and for influencing plant growth, which comprises allowing a herbicidally active amount of a pyridylsalicylaldehyde or —salicylic acid derivative of the formula I as defined in claim 1 to act on the plants and/or their environment.

* * * * *

UNITED STATES PATENT AND TRADEMARK OFFICE
CERTIFICATE OF CORRECTION

PATENT NO.: 5,783,521

DATED: July 21, 1998

INVENTOR(S): RHEINHEIMER et al.

It is certified that error appears in the above-identified patent and that said Letters Patent is hereby corrected as shown below:

On the cover page, insert the following priority information:

-- [30]  Foreign Application Priority Data
  Nov. 2, 1993  [DE]  Germany ............ P 43 37 323.2--.

Col. 41, claim 1, line 10, "alkynyloxy- carbonyl" should be --alkynyloxycarbonyl--.

Signed and Sealed this

Twenty-seventh Day of October, 1998

Attest:

BRUCE LEHMAN

Attesting Officer         Commissioner of Patents and Trademarks